(12) United States Patent
Gamache et al.

(10) Patent No.: US 7,216,528 B2
(45) Date of Patent: May 15, 2007

(54) DIAPHRAGM-SEALED VALVE, ANALYTICAL CHROMATOGRAPHIC SYSTEM AND METHOD USING THE SAME

(75) Inventors: Yves Gamache, Adstock (CA); André Fortier, Adstock (CA)

(73) Assignee: Mecanique Analytique Inc., Thetford Mines, Quebec (CA)

( * ) Notice: Subject to any disclaimer, the term of this patent is extended or adjusted under 35 U.S.C. 154(b) by 0 days.

(21) Appl. No.: 11/064,501

(22) Filed: Feb. 22, 2005

(65) Prior Publication Data
US 2006/0185419 A1 Aug. 24, 2006

(51) Int. Cl.
*G01N 30/04* (2006.01)
*F16K 7/14* (2006.01)

(52) U.S. Cl. .................... 73/23.41; 73/23.42; 137/597; 137/240

(58) Field of Classification Search ............... 73/23.41, 73/23.42, 61.56; 137/597, 240
See application file for complete search history.

(56) References Cited

U.S. PATENT DOCUMENTS

| | | | |
|---|---|---|---|
| 3,019,815 A * | 2/1962 | Nelson et al. ............... 137/883 |
| 3,085,440 A | 4/1963 | Guenther |
| 3,111,849 A | 11/1963 | Broerman |
| 3,139,755 A | 7/1964 | Reinecke et al. |
| 3,140,615 A | 7/1964 | Broerman |
| 3,198,018 A | 8/1965 | Broerman |
| 3,376,894 A * | 4/1968 | Broerman ............... 137/625.48 |
| 3,387,496 A | 6/1968 | Broerman |
| 3,417,605 A | 12/1968 | Hahn |
| 3,439,542 A | 4/1969 | McCray |
| 3,492,873 A | 2/1970 | Broerman et al. |
| 3,545,491 A | 12/1970 | Broerman |
| 3,633,426 A | 1/1972 | Broerman |
| 4,112,766 A | 9/1978 | Ragains |
| 4,276,907 A | 7/1981 | Broerman |
| 4,333,500 A | 6/1982 | Broerman |
| 4,353,243 A * | 10/1982 | Martin ............... 73/23.42 |
| 4,852,851 A * | 8/1989 | Webster ............... 251/61.1 |
| 4,976,750 A | 12/1990 | Munari |
| 5,601,115 A | 2/1997 | Broerman |
| 5,765,591 A * | 6/1998 | Wasson et al. ............... 137/597 |
| 5,927,332 A * | 7/1999 | Richard ............... 137/625.4 |
| 5,952,556 A | 9/1999 | Shoji |
| 6,202,698 B1 | 3/2001 | Stearns |
| 6,227,034 B1 | 5/2001 | Trochesset |
| 6,250,332 B1 * | 6/2001 | Backlund ............... 137/597 |
| 6,453,725 B1 * | 9/2002 | Dahlgren et al. ........... 73/23.42 |

OTHER PUBLICATIONS

U.S. Appl. No. 10/957,560, not yet published, Gamache et al.
"Model Eleven Diaphragm Valve for Process Gas Chromatography", Optichrom Process Chromatograph, 4 p.

* cited by examiner

*Primary Examiner*—Michael Cygan
(74) *Attorney, Agent, or Firm*—Darby & Darby

(57) ABSTRACT

There is provided a diaphragm sealed valve particularly advantageous in chromatographic systems. The valve is provided with first and second body and a seal member compressibly positioned therebetween. The first body comprises a first, a second and a common port, each opening and being interconnected to the others in a recessed fluid communication channel extending in a first interface of the first body. The valve is also provided with first and second plungers, each having a closed position wherein the plunger presses down the seal member against the seat of the corresponding port for closing said corresponding port, and an open position wherein the plunger extends away from the seat for allowing a fluid communication between the corresponding port and the channel. Complex valves are also provided as well as chromatographic systems and methods.

25 Claims, 42 Drawing Sheets

SAMPLE IN SL

ALL PORTS CLOSED

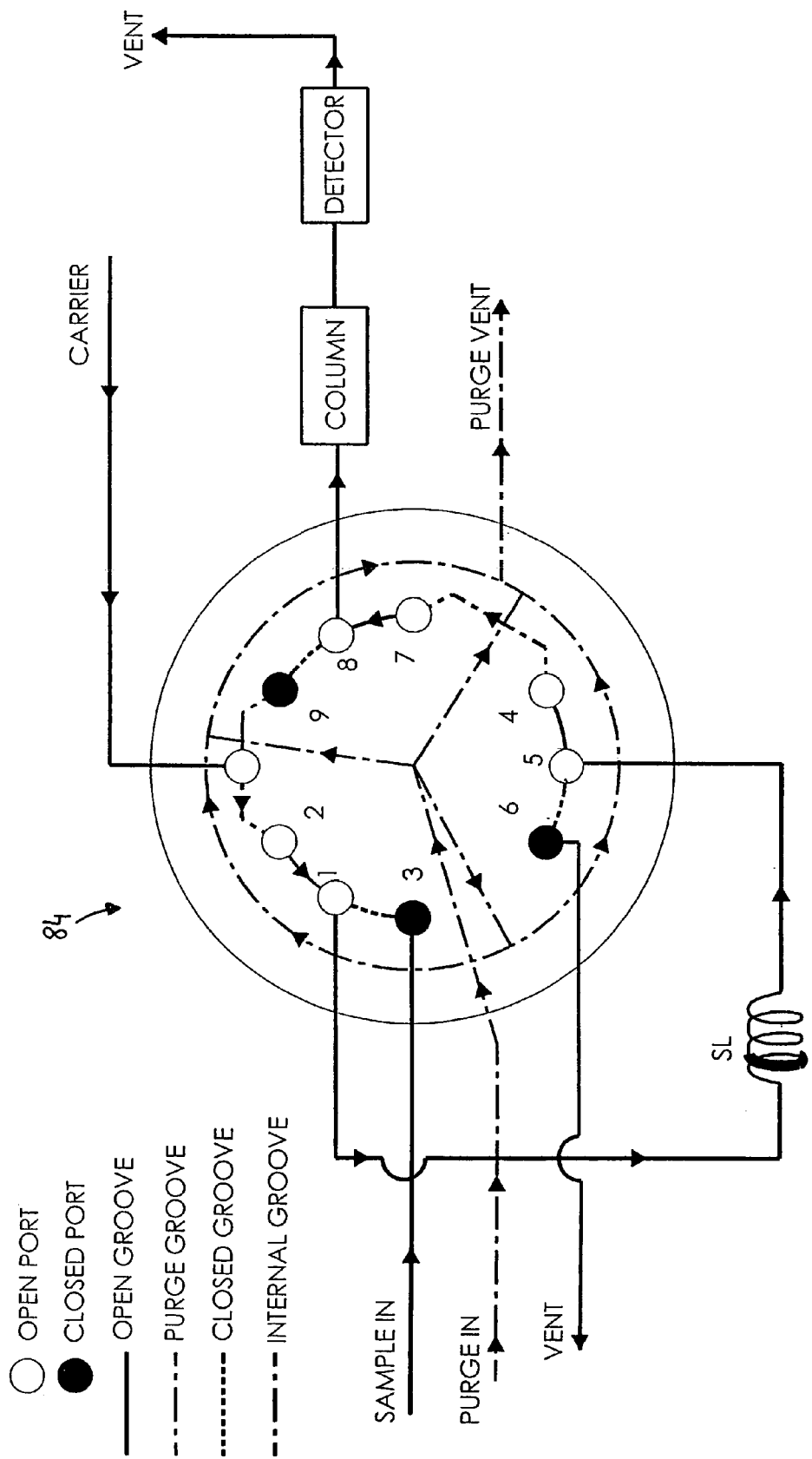

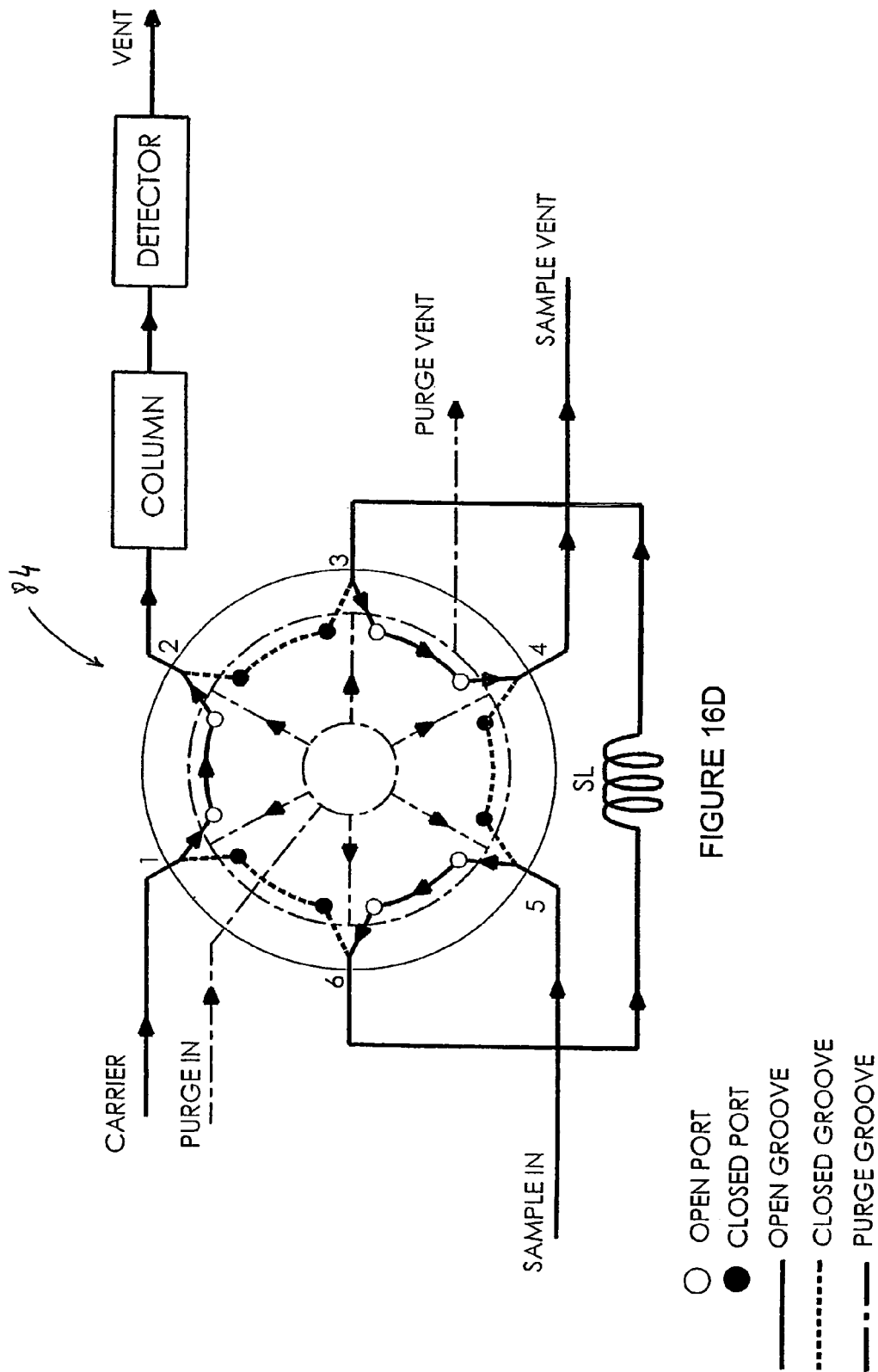

DIAPHRAGM-SEALED VALVE, ANALYTICAL CHROMATOGRAPHIC SYSTEM AND METHOD USING THE SAME

FIELD OF THE INVENTION

The present invention generally relates to a diaphragm-sealed valve for fluid analytical systems, and more particularly concerns a diaphragm-sealed valve having improved characteristics. The present invention also concerns an analytical chromatographic system and an analytical chromatographic method using such a diaphragm-sealed valve.

BACKGROUND OF THE INVENTION

As well known from people involved in the art, chromatographic systems rely on the use of valves to allow reproducible sample introduction and various column switching schemes.

Today, in the chromatographic field, there are mainly two types of valves used: the rotary valves and the diaphragm-sealed valves. The rotary type, as the name suggests, uses a rotary movement to switch or divert various flow paths required for a particular application. Description of such valves may be found in U.S. patent application Ser. No. 10/957,560 filed on Oct. 1, 2004 by the same Applicant.

The rotary chromatographic valves are well suited for liquid applications, even if they are also suitable for gas applications. Their design allows the use of various materials to provide inertness or very long lifetime, and relatively high working pressure and temperature which can be required in various liquid chromatography applications. The actuating means used to actuate a rotary valve is generally a pneumatic rotary one or an electrical motor equipped with some gear to increase the torque needed to rotate the valve. In both cases, these assemblies, i.e. actuating means and valve, require a relatively large amount of room in a system. Furthermore, in cases where a pneumatic actuator is used, extra 3-way solenoid valves must be used to allow pneumatic gas to be switched.

In the bulk gas analysis like He, H2, O2, N2, Ar, Kr, Xe, Ne, CO, CO2, CH4, THC, H2O and some other gases, the working pressure and temperature of the chromatographic system is relatively low compared to liquid chromatography. A diaphragm-sealed chromatographic valve could therefore be used since it is generally well suited for gas chromatography. It would so be advisable and beneficial to use diaphragm-sealed valves instead of rotary valves for gas chromatography wherein the design of a rotary valve may probably be overkilled for low pressure and temperature application in gas chromatography.

A diaphragm-sealed chromatographic valve that would take much less room than a rotary system and that could be built at a lower cost, mainly when compared to rotary valves using ceramic material, while providing a long working lifetime would therefore be very desirable.

For the last forty years, many people have designed diaphragm valves for chromatography. Such diaphragm valves have been used in many commercially available gas chromatographs. They are able to be integrated more easily in a gas chromatograph due to their physical size and since the actuator is embedded in the valve itself. These characteristics make them attractive for gas chromatograph manufacturers. However, their performances are poor. For example, the leak rate from port to port is too high and thus limits the system performance. Moreover, the pressure drop on the valve's ports differs from port to port, causing pressure and flow variation in the system. This causes detrimental effect on column performance and detector baseline. Furthermore, many of them have too much inboard contamination. Such valve designs are shown in U.S. Pat. Nos. 3,111,849; 3,140,615; 3,198,018; 3,376,894; 3,387,496; 3,417,605; 3,439,542; 3,492,873; 3,545,491; 3,633,426; 4,112,766; 4,276,907; 4,333,500; 5,601,115 and 6,202,698. The general concept of these valves is shown in FIG. 1.

As illustrated in FIG. 1, the valve 1 is provided with a top block 2 having an interface 4 and a plurality of ports 6. Each of the ports 6 opens at the interface 4 and has an inclined thread passage 8 to connect various analytical fitting and tubing (not shown). At the bottom of the inclined thread passage 8, there is a conduit 10 extending in the top block 2 and opening at the interface 4. The ports 6 are arranged on a circular line on the interface 4 of the top block 2. The interface 4 is advantageously flat and polished to minimize leaks between port and from ambient atmosphere. The valve 1 is also provided with a bottom block 12 and a diaphragm 14, which is generally made of polyimide, Teflon or other polymer material. The diaphragm 14 is positioned between the top block interface 4 and the bottom block 12. The valve 1 is also provided with a plurality of plungers 16, each being respectively arranged to be able to compress the diaphragm 14 against the top block 2 at a position located between two of the ports 6. Preferably, as illustrated, when the valve is at rest, three plungers 16 are up while the three others are down. When the plungers are up, they compress the diaphragm 14 against the top block 2 for closing the conduits made by diaphragm recess 18, so that fluid circulation is blocked. Alternatively, there is fluid flowing between the ports where the corresponding plungers are down. The recess 18 in the diaphragm 14 sits down in the recess 20 made in the bottom block 12, thereby allowing some clearance for fluid circulation. The bottom block 12 keeps the plungers 16 and the actuating mechanism in position.

Referring now to FIG. 2A, there is shown a typical chromatographic application wherein a sample is injected on a separation column to separate the impurities and then to measure them by the integration of successive signal peaks by the detector, as well known in the art. In FIG. 2A, the sample loop SL is swept by the sample gas, while the separation column and the detector are swept by the carrier gas, coming from the valve port #2. To allow this flow path through the valve, the plungers B, D and F are down while the plungers A, C and E are up. The mechanical equivalent of this valve position is shown in FIG. 2B. To do a sample injection, all valve ports must first be isolated from each other to avoid cross port leaks that invariably lead to inaccurate measurements. This is done by setting plungers B, D and F in the up position. The valve analytical flow path and mechanical equivalent of this valve position is shown in FIGS. 3A and 3B. This step is only a temporary intermediate one. Its time duration depends on the actuating mechanism used and the required actuating pneumatic pressure. Then, the sample loop is put in the carrier circuit. This step is generally known as the sampling loop injection position. This is done by moving down plungers A, C and E while keeping plungers B, D and F in the up position. This position is shown on FIG. 4A and the mechanical one in FIG. 4B. In a similar way, to come back in the sampling position which is illustrated in FIG. 2A, the plungers A, C and E are first brought back in the up position. This leads to the intermediate position shown in FIG. 3A, i.e. all plungers up. Finally, the plungers B, D and F are brought back down. So, the valve is now in the position shown in FIG. 2A, i.e. sampling loop filling position. All the patents that we previously referred use this general concept or some slight variation thereof.

Referring again to FIG. 1, the main aspect of this concept is to interrupt the flow between two adjacent ports. For that, the corresponding plunger presses the diaphragm 14, which is then pressed on the interface 4 of the top block 2. Thus, the sealing relies simply on the surface of the plunger defining the area that presses the diaphragm recess 18 on the interface 4. This technique imposes tight tolerances on the surface finish, surface flatness and the plungers' length. Any scratch on the interface 4 or imperfection of the diaphragm 14 will generate leaks. Moreover, the length of all plungers must be the same. Any difference in their lengths will result in leaks, since a shorter plunger will not properly compress the diaphragm against the interface 4. In the prior art, there are some variations of this general concept. The main one relates to the location of the bottom block recess 20. In the past, this recess 20 or its equivalent was located internally in the top block 2, or on its interface 4. U.S. Pat. Nos. 3,111,849; 3,198,018; 3,545,491; 3,633,426 and 4,112,766, which were granted to the same group of people, illustrate this concept. However, as they reported in a more recent valve brochure specification entitled "Applied Automation Company, series 11 diaphragm valve", this method has been dropped because of a too high cold flow. Cold flow is also often referred to as cross port flow leak. Their latest design, which was commercialized, uses a flat and polished interface 4 on the top block 2 and a recess 20 in the bottom block 12. In this design, the diaphragm 14 has no recess. Moreover, in order to reduce the cold flow, it was also envisaged to use two diaphragms. In fact, as disclosed in U.S. Pat. No. 3,111,849, the use of a "cushion" diaphragm helps to compensate for any slight non-parallelism or length difference of plungers. Other attempts have also been made to correct the non-parallelism, as disclosed in U.S. Pat. Nos. 3,376,894; 3,545,491 and 3,633,426, wherein the use of solid plungers has been replaced with the use of small steel balls.

The concern about plunger length has also been taken into consideration in U.S. Pat. No. 6,202,698, granted to Valco Company, which suggests the use of plungers made of softer material. This allows tolerance reduction for the length of such plungers.

However, such designs still result into too much leak rate between ports since the sealing done by the plungers' pressure is not equal on diaphragm.

Other attempts have been made in the past to eliminate problems caused by plunger tolerance variations. U.S. Pat. No. 3,139,755 discloses a valve wherein no plunger is used. Instead, a hydraulic pressure is used. However, an auxiliary source of pressure must be used since the pneumatic amplification of pneumatic actuating mechanism does not exist. The system, as far as we know, wasn't commercialized. Cross port leaks are still an important problem.

Another design is disclosed in U.S. Pat. No. 3,085,440. In this valve, the diaphragm has been replaced by an O-ring. Nevertheless, cross port leaks are still too high for modern high sensitivity detector.

In brief, in view of the previously mentioned patents, it can be seen that many attempts have been made to try fixing cross port leaks problems and outboard or inboard contamination. All of the proposed designs are quite similar in regard to sealing mechanisms and have the same drawbacks. For example, U.S. Pat. No. 3,140,615, granted in 1964, and U.S. Pat. No. 6,202,698, granted in 2001, do use the same sealing concept in regard to flow switching between ports.

Valco Company did release the DV series valve wherein the diaphragm 14 has an additional recess 18 as illustrated in FIG. 1. The recess 18 sits down in the recess 20 of the bottom block 12. So, when a plunger 16 is in down position, the diaphragm recess 18 sits in the bottom block recess 20, thereby clearing the passage between two adjacent ports, reducing the pressure drop and helping to operate with a low pressure sample.

Finally, it can be seen from the various brochures used to market these valves that the lifetime of these valves is mostly stated in terms of actuations. Most of the time, the number of actuations stated is between 500,000 and 1,000,000. However, it appears that this specification is related to the actuating mechanism and not to the leak rate of the valve. In this aspect, the diaphragm type valve's specifications are not as well defined as the rotary type valve, wherein it is clear that the lifetime of the valve is expressed in terms of leaks.

Besides, a brand new diaphragm valve will often have too many leaks between ports for low level applications. Moreover, it appears that when the valve is at rest for a long period of time, it doesn't perform well when put back in service. This is caused by the diaphragm getting compressed and marked where the plungers press it. It is even worst for valves having fine edge plungers defining a ring type sealing surface.

Thus, the diaphragm type gas chromatography valves of the prior art have several disadvantages: they present too much cross port leaks and too much pressure drop on selected adjacent ports. Moreover, they are difficult to operate when sample pressure is low and they cannot conveniently work with sub-atmospheric sample pressure. Furthermore, they rely on tight tolerance of plungers' length, to minimize cross port leaks.

Therefore, it would be desirable to provide a diaphragm-sealed valve that would overcome the above-mentioned drawbacks of the diaphragm valves of the prior art while being less expensive to manufacture.

SUMMARY OF THE INVENTION

An object of the present invention is to provide a diaphragm-sealed valve that satisfies the above-mentioned needs.

Accordingly, the present invention provides a diaphragm-sealed valve comprising a first body having a first interface. The first interface is provided with a recessed fluid communication channel extending therein. The first body has a first, a second and a common fluid port. Each of the ports opens into the recessed fluid communication channel for interconnecting each of the ports together through the fluid communication channel. Each of the first and second ports is provided with a seat disposed so as to allow fluid communication therearound within the communication channel. The diaphragm-sealed valve is also provided with a second body interconnected with the first body and having a second interface facing the first interface. The second body has a first and a second passage, each of the passages facing one of the first and second ports respectively. The diaphragm-sealed valve is also provided with a seal member compressibly positioned between the first and second interfaces. The seal member has a shape adapted to cover the first and second ports. The diaphragm-sealed valve is also provided with a first and a second plunger, each being respectively slidably disposed in one of the passages of the second body. Each of the plungers has a closed position wherein the corresponding plunger presses down the seal member against the seat of the corresponding port for closing the corresponding port, and an open position wherein the plunger extends away from the seat of the corresponding port for allowing a fluid communication between the corresponding port and the channel. The diaphragm-sealed valve is also provided with actuating means for actuating each of the plungers between the closed and open positions thereof.

In a preferred embodiment of the present invention, the actuating means independently actuate each of the plungers.

According to another aspect of the invention, there is also provided an analytical chromatographic system having a diaphragm-sealed valve as defined above and further having a purge circulation line. The purge circulation line comprises an annular recess extending in the first interface and surrounding the fluid communication channel. The purge circulation line also has a fluid inlet and a fluid outlet, each having an opening lying in the annular recess for providing a continuous fluid flow in the annular recess. The analytical chromatographic system is also provided with monitoring means operatively connected to the fluid outlet for monitoring a fluid passing therethrough.

In a preferred embodiment of the analytical chromatographic system, the monitoring means are adapted to monitor the fluid continuously.

In a further preferred embodiment of the present invention, there is also provided another diaphragm-sealed valve comprising a first body having a first interface. The first interface is provided with a plurality of distinct recessed fluid communication channels extending therein. The first body has a plurality of port sets, each comprising a first, a second and a common fluid port. Each port of a corresponding set opens into a corresponding one of the recessed fluid communication channels respectively for interconnecting each port of the corresponding set together through the corresponding fluid communication channel respectively. Each of the first and second ports of each of the sets is provided with a seat disposed so as to allow fluid communication therearound within the corresponding communication channel. The diaphragm-sealed valve is also provided with a second body interconnected with the first body and having a second interface facing the first interface. The second body has a plurality of passage pairs, each comprising a first and a second passage. Each passage of a corresponding pair respectively faces one of the first and second ports of a corresponding set. The diaphragm-sealed valve is also provided with a seal member compressibly positioned between the first and second interfaces. The seal member has a shape adapted to cover each of the first and second ports of all of the port sets. The diaphragm-sealed valve is also provided with a plurality of pairs of first and second plungers, each plunger of a corresponding pair being respectively slidably disposed in one of the passages of a corresponding pair. Each of the plungers has a closed position wherein the corresponding plunger presses down the seal member against the seat of the corresponding port for closing the corresponding port, and an open position wherein the plunger extends away from the seat of the corresponding port for allowing a fluid communication between the corresponding port and a corresponding channel. The diaphragm-sealed valve also has actuating means for actuating each of the plungers between the closed and open positions thereof.

According to another aspect of the invention, there is also provided an analytical chromatic method comprising the steps of:

a) providing a fluid sampling system comprising a diaphragm-sealed valve provided with a plurality of independently actuated ports serially interconnected to each other. The fluid sampling system is further provided with a sample inlet, a carrier inlet, a sampling loop having an inlet and an outlet, a sample vent line and analytical means provided with an inlet, each being operatively interconnected to the valve through a corresponding one of said ports;

b) providing fluid communication from the sample inlet to the inlet of the sampling loop by actuating the corresponding ports, thereby providing a fluid sample in the sampling loop;

c) closing the outlet of the sampling loop by actuating the corresponding port to isolate the sampling loop;

d) providing fluid communication from the carrier inlet to the inlet of the sampling loop by actuating the corresponding port to pressurize the sampling loop;

e) preventing fluid communication from each of the ports to the remaining ports by actuating the corresponding ports; and f) providing fluid communication from the outlet of the sampling loop to the inlet of the analytical means by actuating the corresponding port, thereby injecting the sample in the analytical means.

BRIEF DESCRIPTION OF THE DRAWINGS

These and other objects and advantages of the invention will become apparent upon reading the detailed description and upon referring to the drawings in which:

FIG. 10F is a schematic representation of the valve shown in FIG. 10A, the valve being in the sample injection position.

FIG. 16D is a schematic representation of another preferred embodiment of the diaphragm-sealed valve of the present invention.

Figure 1:
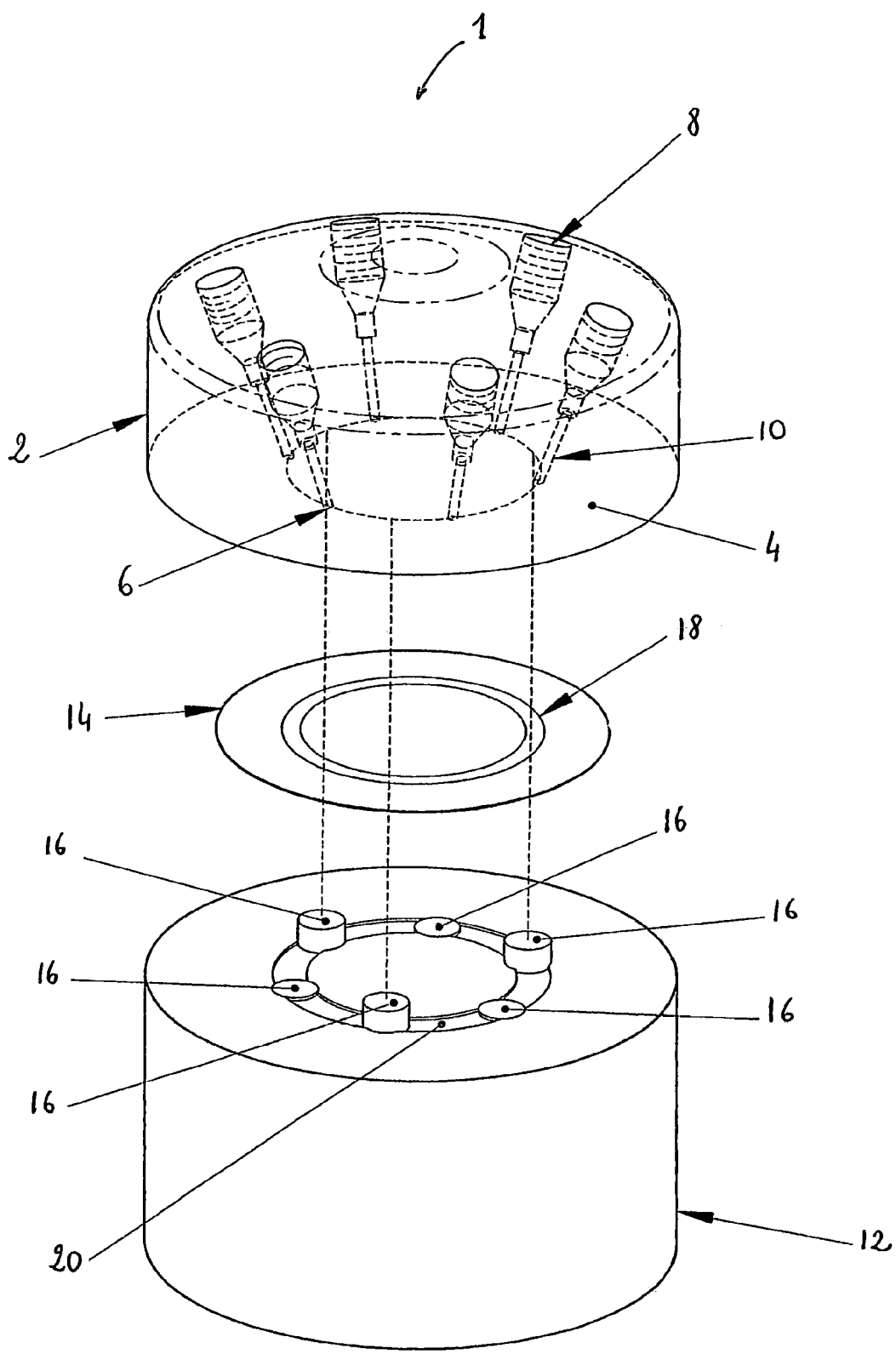
FIG. 1 (PRIOR ART) is an exploded perspective view of a diaphragm-sealed valve known in the art.

While the invention will be described in conjunction with example embodiments, it will be understood that it is not intended to limit the scope of the invention to such embodiments. On the contrary, it is intended to cover all alternatives, modifications and equivalents as may be included as defined by the appended claims.

DESCRIPTION OF PREFERRED EMBODIMENTS

In the following description, similar features in the drawings have been given similar reference numerals and, in order to weight down the figures, some elements are not referred to in some figures if they were already identified in a precedent figure.

The present invention concerns a diaphragm-sealed valve, also referred to as a diaphragm based tight shut off valve, mostly dedicated for analytical equipments, and more particularly chromatographic equipments or on line analyzers. The present invention also concerns chromatographic systems and chromatographic methods based on the use of at least one diaphragm-sealed valve. As will be greater detailed herein below, these systems and methods are based on the use of at least one diaphragm-sealed valve, which, in a first preferred embodiment can be referred to as a three way switching cell. This switching cell has one common port and two actuated ports, these actuated ports being advantageously independently actuated. Thus, each of the independently actuated ports is preferably independently controlled in a way that both could be open or closed at the same time or one could be open while the other is closed and vice versa. Moreover, the fluid flowing through the common port could be allowed to flow to or from any one of the independently actuated ports at the same time or in a predetermined sequence.

In preferred embodiments of the present invention which will be described below, a plurality of three way switching cells are advantageously used to allow more complex flow path switching schemes. By interconnecting together various switching cells, a typical chromatographic diaphragm valve could be done. In the case an elementary cell is used, the switching steps could be: make before break, break before make, all ports opened or all ports closed. These switching steps are not available with standard three way valves.

Figures 5A, 5B:
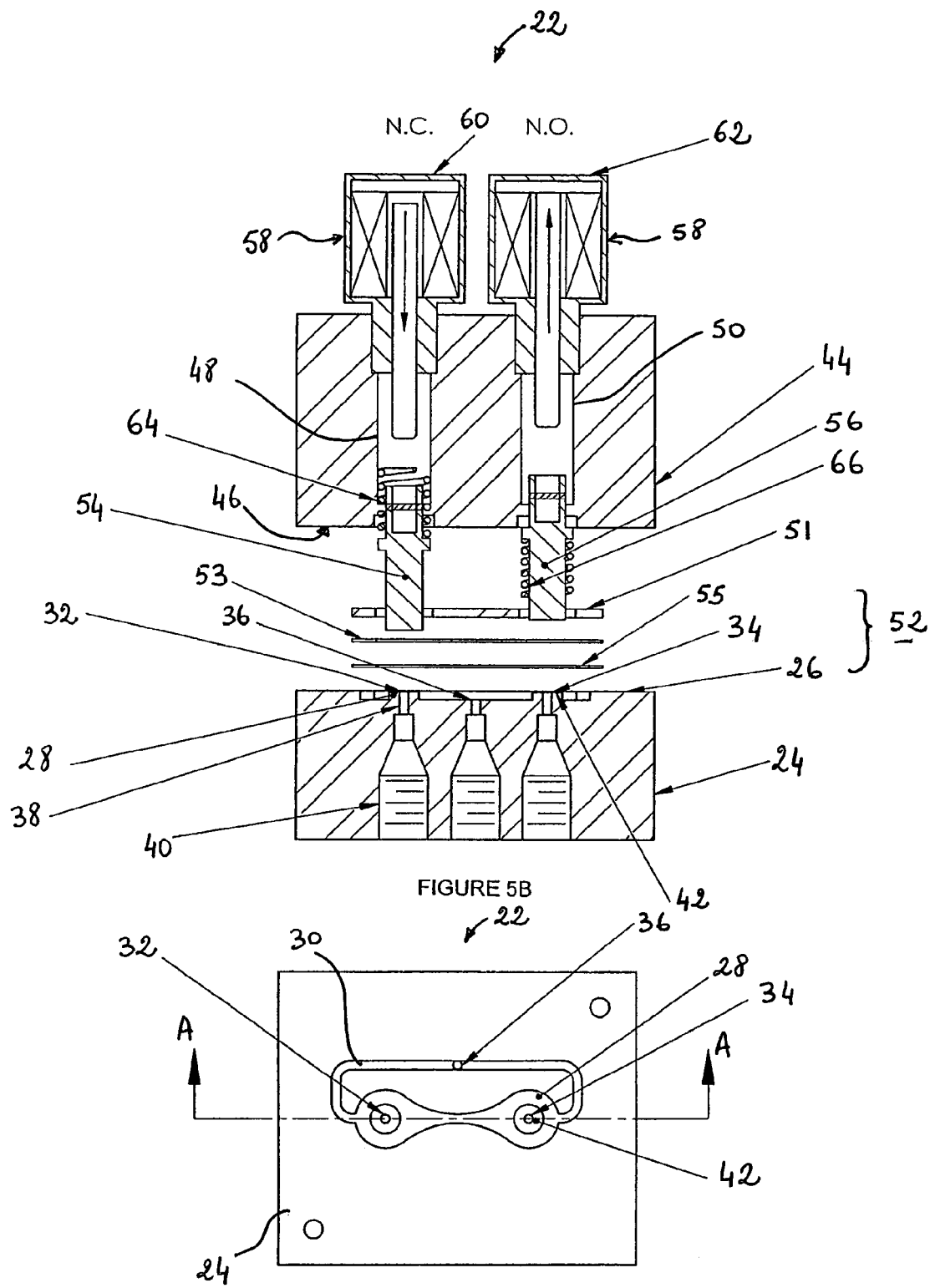
FIG. 5A is a top view of a preferred embodiment of the first body of a diaphragm-sealed valve of the present invention.
FIG. 5B is a cross-sectional side view taken along line A—A of the diaphragm-sealed valve shown in FIG. 5A.

Referring to FIGS. 5A and 5B, there is shown a first preferred embodiment of the present diaphragm-sealed valve, which can be referred to as a three way switching cell. The illustrated diaphragm-sealed valve 22 is provided with a first body 24 having a first interface 26 provided with a recessed fluid communication channel 28 extending therein. The recessed fluid communication channel 28 preferably has a loop shaped portion 30. The first body 24 has a first, a second and a common fluid port, respectively 32, 34 and 36. As known in the art, each of the ports is preferably provided with a fluid passage 38 connected to a threaded hole 40 providing tubing connections. Each of the ports 32, 34, 36 opens into the recessed fluid communication channel 28 for interconnecting each of the ports together through the fluid communication channel 28, which acts as a fluid conduit. Each of the first and second ports 32, 34 is provided with a seat 42 disposed so as to allow fluid communication therearound within the communication channel 28. Preferably, and as illustrated, the seat 42 of each of the first and second ports 32, 34 has a raised portion, which can preferably extend at the interface level 26. More preferably, the raised portions of the seats 42 of the ports 32, 34 are lower than the interface 26 to give room for the seal member 52 vertical movement, as will be greater detailed below. The diaphragm-sealed valve 22 is also provided with a second body 44 interconnected with the first body 24, preferably by any convenient attaching means known in the art such as a set of screws (not shown). The second body 44 has a second interface 46 facing the first interface 26. The second body 44 also has a first and a second passage 48, 50. Each of the passages 48, 50 faces one of the first and second ports 32, 34 respectively. The valve 22 is also provided with a seal member 52 compressibly positioned between the first and second interfaces 26, 46. The seal member 52 has a shape adapted to cover the first and second ports 32, 34, and advantageously the entire fluid communication channel 28 to act as a seal for inboard or outboard contaminations. This seal member 52 allows to provide a flow interruption through the corresponding port 32 or 34, when it is pressed against the seat 42 of the port. Preferably, the seal member 52 has a polymer diaphragm 55 and each of the first and second interfaces 26, 46 has a planar and circular shape. More preferably, the seal member 52 has a Teflon spacer 51, a metallic diaphragm 53 which is advantageously a stainless diaphragm, and a polymer diaphragm 55. Each of these elements is advantageously arranged in a stacked relationship, the polymer diaphragm 55 being pressable against the seat 42 of each of the first and second ports 32, 34. The valve 22 is also provided with a first and a second plunger 54, 56, each being respectively slidably disposed in one of the passages 48, 50 of the second body 44. Each of the plungers 54, 56 has a closed position wherein the corresponding plunger presses down the seal member 52 against the seat 42 of the corresponding port 32, 34 for closing the corresponding port, and an open position wherein the plunger extends away from the seat 42 of the corresponding port 32, 34 for allowing a fluid communication between the corresponding port and the channel 28. In this preferred embodiment, the Teflon spacer is advantageously provided with a first and a second hole, each for respectively slidably receiving one of the plungers 54, 56. The valve 22 also has actuating means 58 for actuating each of the plungers 54, 56 between the closed and open positions thereof. Preferably, the actuating means 58 independently actuate each of the plungers 54, 56. More preferably, the actuating means 58 advantageously have a first and a second solenoid 60, 62, each respectively actuating one of the first and the second plungers 54, 56. Nevertheless, it should be noted that any other actuating means that advantageously allow an independent actuation of the plungers 54, 56 could also be envisaged as will be greater detailed thereinafter. Preferably, and as illustrated, the actuating means 58 advantageously have first and second resilient means, preferably a first and a second spring 64, 66, each being respectively mounted on a corresponding plunger 54, 56 for biasing the corresponding plunger. Each of the spring 64, 66 can advantageously be mounted in two different positions, thereby providing a predetermined resting position for each of the plungers 54, 56. Thus, different valve configurations can advantageously be obtained at power off. Both plungers 54, 56 can be forced up or down. In the illustrated preferred embodiment, the spring 64 associated with the solenoid 60 is mounted to force the plunger 54 down while the spring 66 associated to the solenoid 62 is mounted to force the plunger 56 up. This results in a configuration normally closed (NC) between port 32 and 36, and normally open (NO) between port 34 and 36, when there is no power on the solenoids 60 and 62.

Figure 6A:
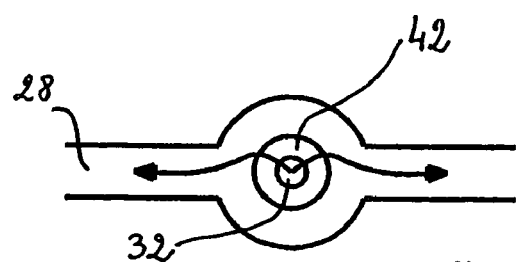
FIG. 6A is a top view of a port of the valve shown in FIG. 5B, the port being in an open position.
Figure 6B:
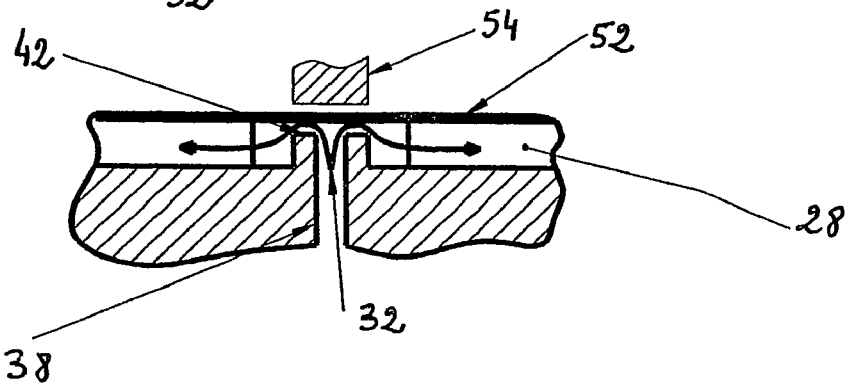
FIG. 6B is a cross-sectional side view of the port shown in FIG. 6A.
Figure 6C:
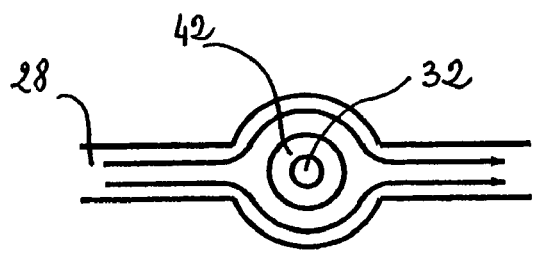
FIG. 6C is a top view of the port shown in FIG. 6A, the port being in a closed position.
Figure 6D:
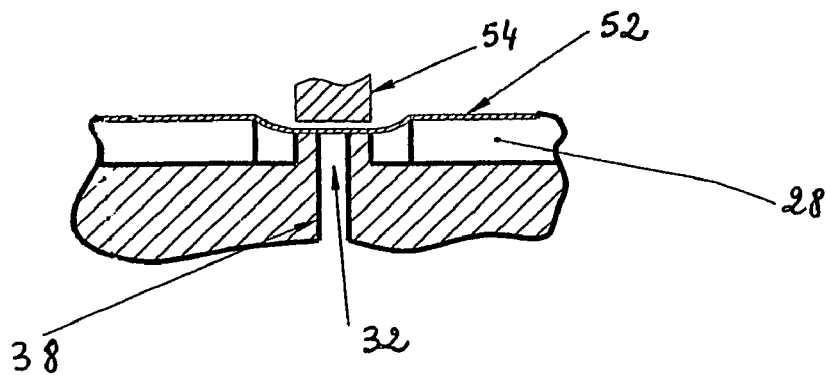
FIG. 6D is a cross-sectional view of the port shown in FIG. 6C.

Referring now to FIGS. 6A to 6D, there is illustrated the working principle of one of the first and second ports 32, 34. In FIGS. 6A and 6B the port 32 is open, so the fluid is allowed to flow through port 32 and then in each direction away from the seat 42. Of course, according to a particular application, the fluid could flow from or to the port 32. In FIGS. 6C and 6D, the port 32 is shown in the closed position. The fluid from the other ports is allowed to flow around the seat 42 in the fluid communication channel 28.

Figure 7A:
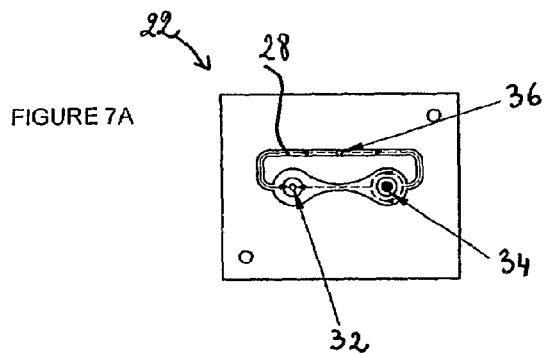
FIG. 7A is a top view of the first body shown in FIG. 5A, the ports being in a predetermined position.
Figure 7B:
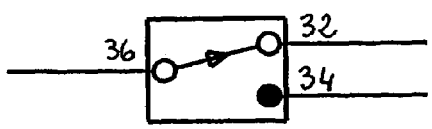
FIG. 7B is a schematic representation of the ports shown in FIG. 7A.
Figure 7C:
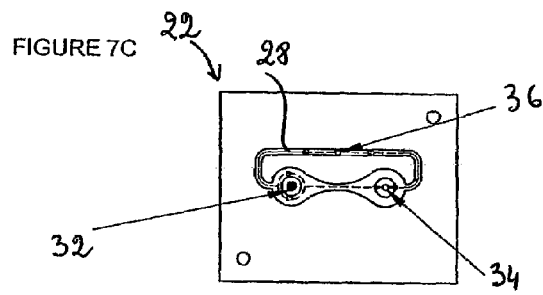
FIG. 7C is a top view of the first body shown in FIG. 5A, the ports being in another position.
Figure 7D:
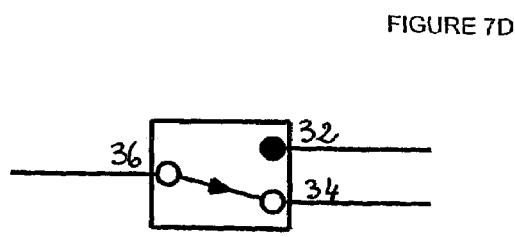
FIG. 7D is a schematic representation of the ports shown in FIG. 7C.
Figure 7E:
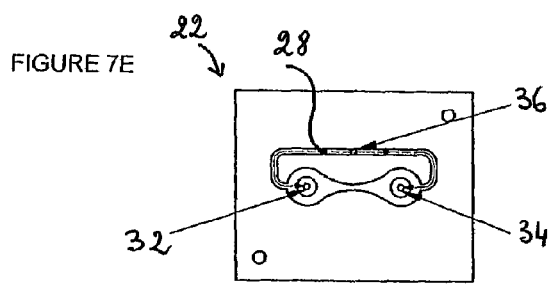
FIG. 7E is a top view of the first body shown in FIG. 5A, the ports being in another position.
Figure 7F:
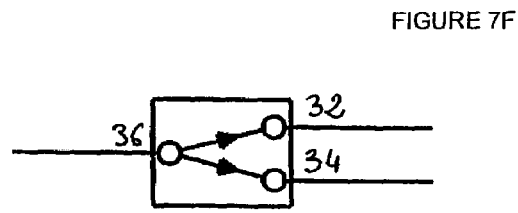
FIG. 7F is a schematic representation of the ports shown in FIG. 7E.
Figure 7G:
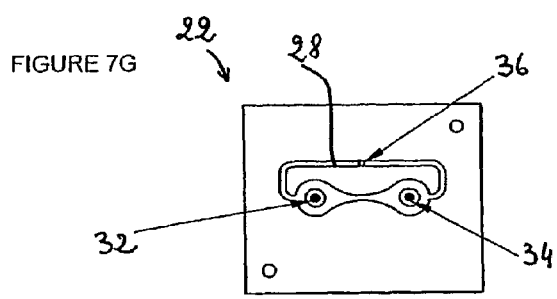
FIG. 7G is a top view of the first body shown in FIG. 5A, the ports being in another position.
Figure 7H:
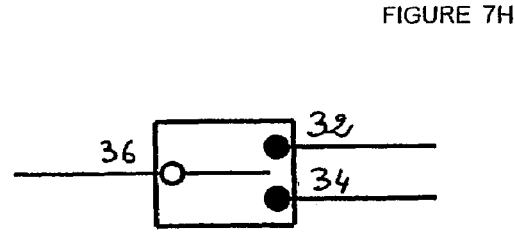
FIG. 7H is a schematic representation of the ports shown in FIG. 7G.

FIGS. 7A to 7H illustrate the different fluid flow paths and the schematic equivalents which can be obtained with the present valve. FIGS. 7A and 7B show the port 32 in the open position while port 34 is in the closed position. FIGS. 7C and 7D show the port 32 closed while the port 34 is opened. FIGS. 7E and 7F show both ports 32, 34 open while FIGS. 7G and 7H show both ports 32, 34 closed.

An important characteristic of the invention can be deducted from FIGS. 6 and 7. In anyone valve positions, there is no dead volume since there is always fluid flowing around the seat 42 and in the loop shaped portion 30 of the fluid communication channel 28. So there is no dead volume effect generated by the valve since the channel 28 always appears like a fluid conduit or tubing.

Another important aspect of the present invention is the independent control of the ports 32 and 34. This allows the different valve positions shown in FIGS. 7A to 7H. Moreover, the valve timing between actuation steps can be easily controlled by a control means (not shown) operatively connected to the actuating means 58. For example, when switching from port 32 to 34, the actuation step could be make before break or break before make.

The fact of sealing the ports 32 and 34 by pressing the diaphragm 52 thereon results in a positive sealing effect. Indeed, it seals completely the port 32 or 34 and totally blocks the fluid flow therefrom or thereinto. So, relatively high pressure could be applied to the ports 32, 34 without generating any leak nor any detrimental impact on the analytical results.

Moreover, in a preferred embodiment, the plungers 54, 56 can advantageously be tied to the diaphragm 52. Thus, when the plunger 54 or 56 is in the open position, it pulls up the diaphragm 52 from the port 32 or 34. This has for effect of clearing completely the corresponding port seat 42. So, there is very little pressure drop on the port and the pressure is similar for any of the ports 32, 34.

Figure 8:
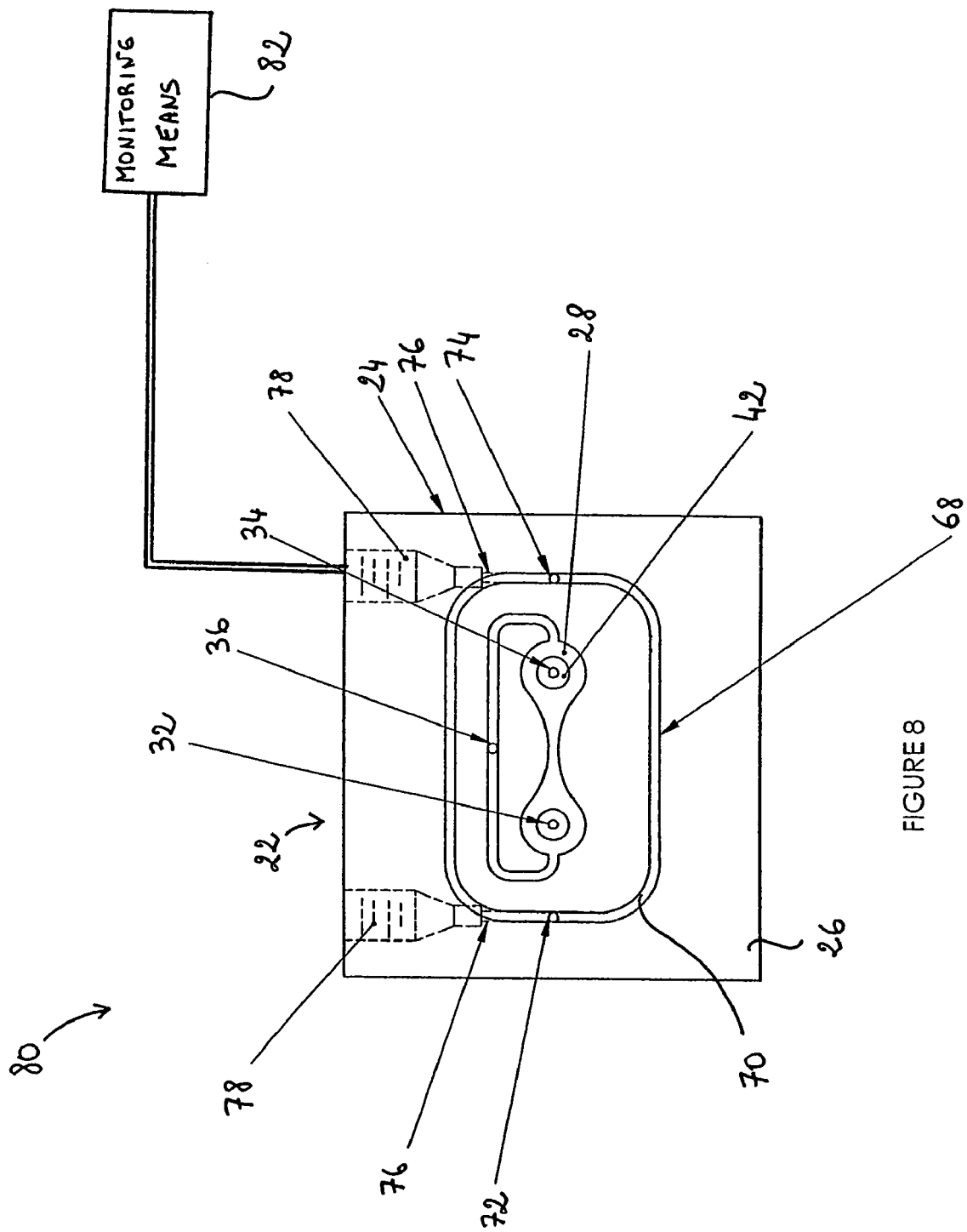
FIG. 8 is a top view of another preferred embodiment of the first body of a diaphragm-sealed valve of the present invention.

Furthermore, the valve of the present invention advantageously allows sub atmospheric pressure operation. Indeed, FIG. 8 shows another preferred embodiment of the present invention, wherein the valve 22 further has a purge circulation line 68. The purge circulation line 68 is provided with an annular recess 70 extending in the first interface 26 and surrounding the fluid communication channel 28. The purge circulation 68 line also has a fluid inlet 72 and a fluid outlet 74, each having an opening lying in the annular recess 70 for providing a continuous fluid flow in the annular recess 70. Preferably, the fluid inlet and outlet 72, 74 are each provided with a fluid passage 76 and an associated threaded hole 78 for allowing tubing connections. Thus, a clean purging fluid can advantageously be allowed to flow through the purge circulation line 68, thereby evacuating any inboard and outboard contamination and any fluid process leak. This concept is detailed in U.S. application Ser. No. 10/957,560, filed on Oct. 1, 2004, whose disclosure is incorporated herein by reference.

Still referring to FIG. 8, the valve of the present invention can also advantageously be used in an analytical chromatographic system 80 to provide a system having improved characteristics. Indeed, such an analytical chromatographic system 80 is advantageously provided with a diaphragm-sealed valve 22 as defined above and provided with a purge circulation line 68. The analytical system 80 is also advantageously provided with monitoring means 82 operatively connected to the fluid outlet 74 for monitoring a fluid passing therethrough. In a preferred embodiment, the monitoring means 82 have a purity detector for detecting contamination of said fluid. Preferably, the monitoring means 82 are adapted to monitor the fluid passing through the purge circulation line 68 continuously.

As already explained, as a first application, the valve could be used as a simple three way type switching valve used to switch between two streams. However, an interesting aspect of the present invention is revealed when we combine together a plurality of elementary switching cells 22 as previously described.

Accordingly, referring now to FIGS. 10A to 10G, there is shown another diaphragm sealed valve according to another preferred embodiment of the present invention which uses a plurality of elementary switching cells 22. Indeed, in this preferred embodiment, the diaphragm-sealed valve 84 is provided with a first body 24 having a first interface 26 provided with a plurality of distinct recessed fluid communication channels 28 extending therein. The first body 24 has a plurality of port sets, each comprising a first, a second and a common fluid port 32, 34, 36. Each port of a corresponding set opens into a corresponding one of the recessed fluid communication channels 28 respectively for interconnecting each port 32, 34, 36 of the corresponding set together through the corresponding fluid communication channel 28 respectively. Each of the first and second ports 32, 34 of each of the sets is provided with a seat 42 disposed so as to allow fluid communication therearound within the corresponding communication channel 28. As already explained with reference to FIGS. 5A and 5B, each of the seats 42 of the first and second ports 32, 34 is preferably lower than the interface 26 for giving sufficient room for the seal member vertical movement. The diaphragm sealed valve 84 is also provided with a second body 44 interconnected with the first body 24 and having a second interface 46 facing the first interface 26. The second body 44 has a plurality of passage pairs, each comprising a first and a second passage 48, 50. Each passage 48, 50 of a corresponding pair respectively faces one of the first and second ports 32, 34 of a corresponding set. The diaphragm sealed valve 84 is also provided with a seal member 52 compressibly positioned between the first and second interfaces 26, 46. The seal member 52 has a shape adapted to cover each of the first and second ports 32, 34 of all of the port sets. Preferably, the sealed member 52 has a polymer disc 55. More preferably, as previously described with reference to FIGS. 5A and 5B the seal member 52 has a Teflon spacer 51, a metallic diaphragm 53 which is advantageously a stainless diaphragm, and a polymer diaphragm 55. Each of these elements is advantageously arranged in a stacked relationship, the polymer diaphragm 55 being pressable against the seat 42 of each of the first and second ports 32, 34. The diaphragm sealed valve 84 is also provided with a plurality of pairs of first and second plungers 54, 56. Each plunger 54, 56 of a corresponding pair is respectively slidably disposed in one of the passages 48, 50 of a corresponding pair. Each of the plungers 54, 56 has a closed position wherein the corresponding plunger presses down the seal member 52 against the seat 42 of the corresponding port 32, 34 for closing the corresponding port, and an open position wherein the plunger extends away from the seat 42 of the corresponding port 32, 34 for allowing a fluid communication between the corresponding port and a corresponding channel 28. The diaphragm sealed valve 84 also has actuating means 58 for actuating each of the plungers 54, 56 between the closed and open positions thereof. Preferably, the actuating means 58 independently actuate each of the plungers 54, 56, as already described above.

Still referring to FIGS. 10A to 10G, in a further preferred embodiment, the valve is further advantageously provided with a purge circulation line 68. The purge circulation line 68 has a looped recessed fluid circuit 86 extending in the first interface 26. The looped fluid circuit 86 has an outer annular recess 88 and an inner recess 90, each extending in the first interface 26. The fluid circuit 86 further has a plurality of separation recesses 92 radially extending in the first interface 26. Each of the separation recesses 92 is connected to each of the outer and inner recesses 88, 90 for defining a plurality of first interface portions 94 isolated from each others. Each of the first interface portions 94 encloses one of the fluid communication channels 28. The fluid circuit 86 is also provided with a fluid inlet 72 and a fluid outlet 74, each having an opening lying at the first interface 26. Each of the inlet and outlet 72, 74 is in continuous fluid communication with a respective one of the outer and inner recesses 88, 90 for providing a continuous fluid flow in the looped recessed fluid circuit 86. This preferred embodiment is particularly advantageous since it allows to continuously monitor the working of the valve for detecting any undesirable contamination and/or leaks. In another further preferred embodiment, as illustrated, each of the first and second ports 32, 34 is advantageously circularly arranged in a port circle 96 concentrical with the first interface 26. In another further preferred embodiment, the actuating means 58 advantageously have a plurality of pairs of first and second solenoids 60, 62, each solenoid of a corresponding pair respectively actuating a corresponding one plunger 54, 56 of a corresponding pair. With the different valve configurations described above, different applications can be envisaged.

Figure 2A:
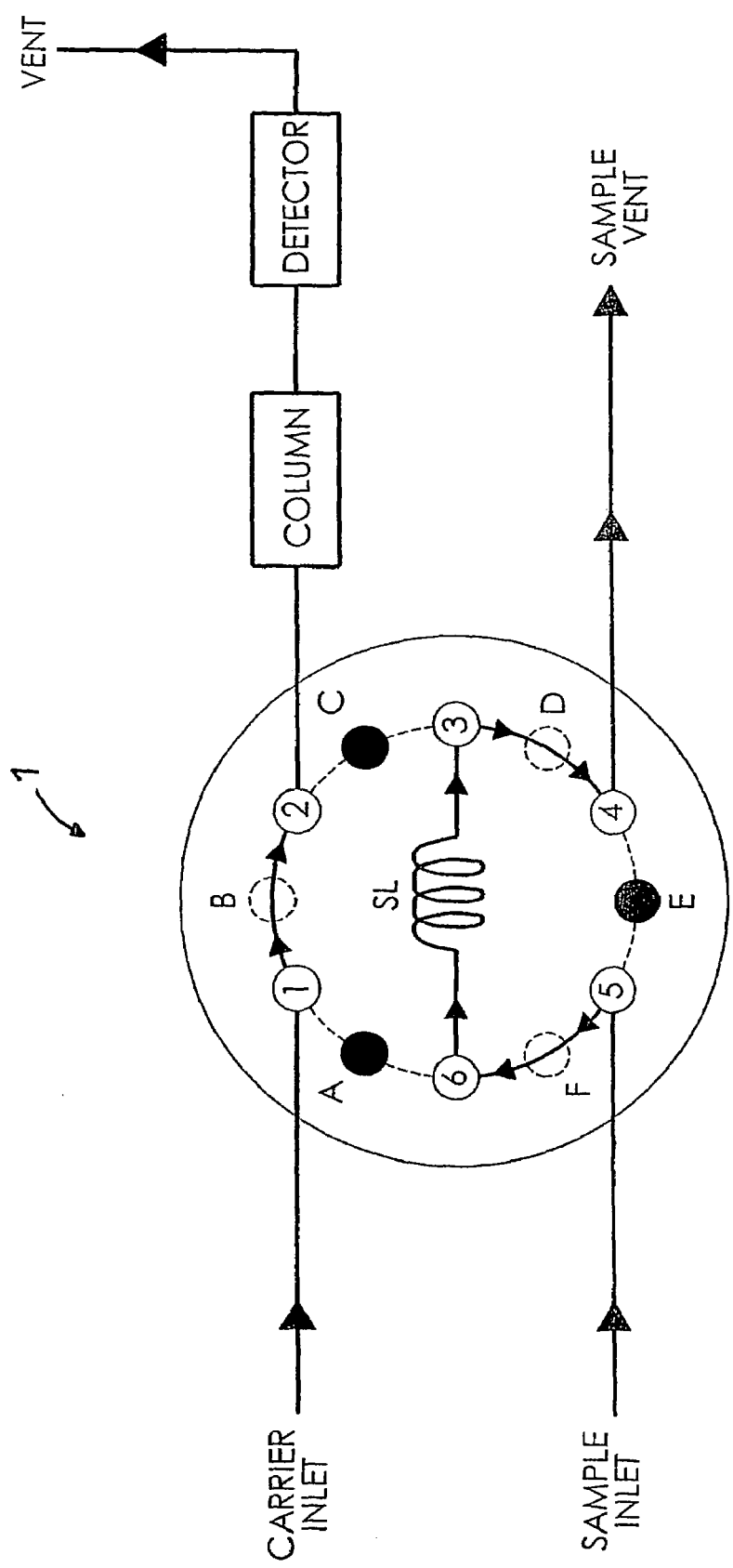
FIG. 2A (PRIOR ART) is a schematic representation of a prior typical chromatographic application using a six-port valve, the valve being in a sampling position.
Figure 2B:
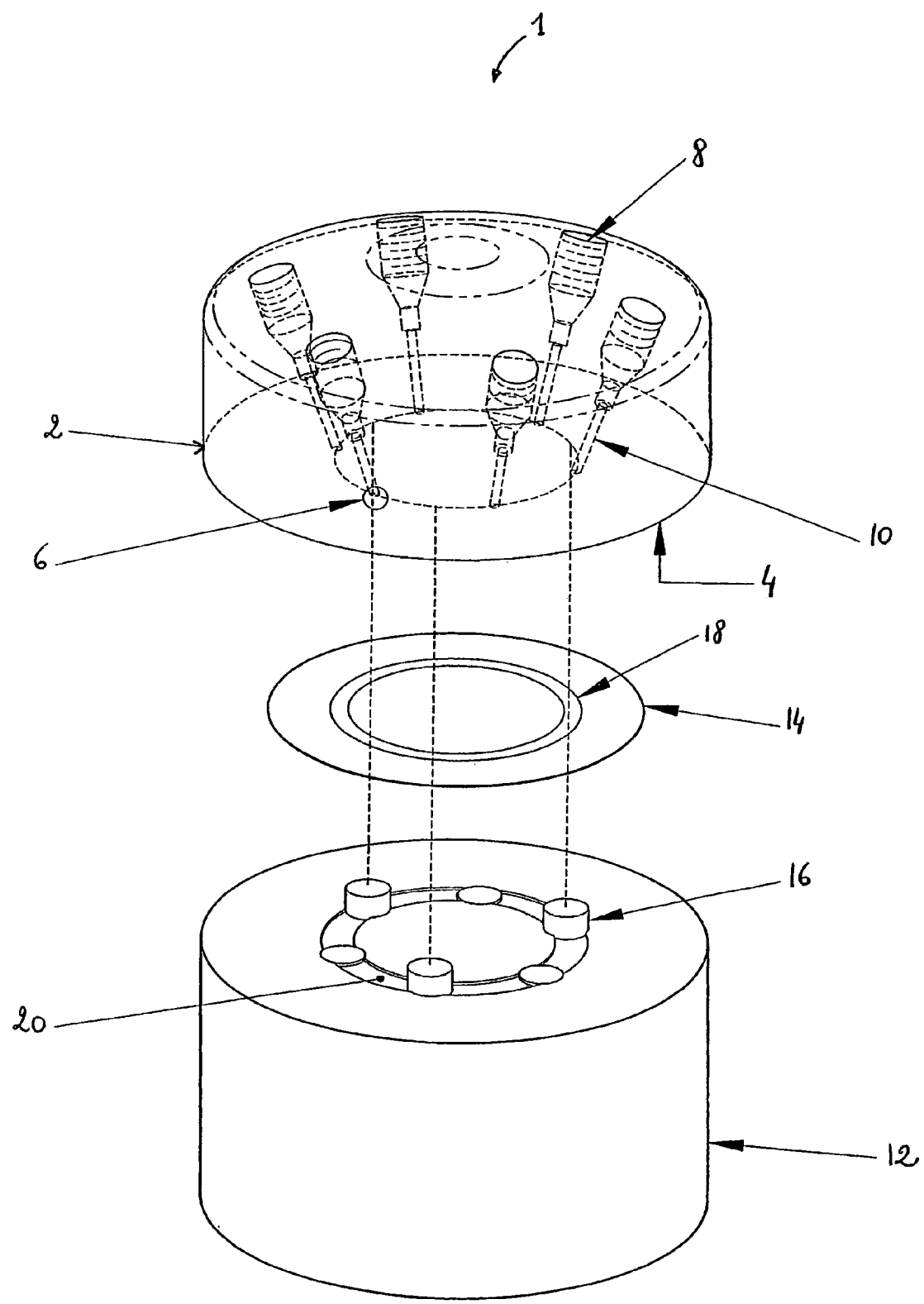
FIG. 2B (PRIOR ART) is an exploded perspective view of the diaphragm-sealed valve shown in FIG. 2A.
Figure 3A:
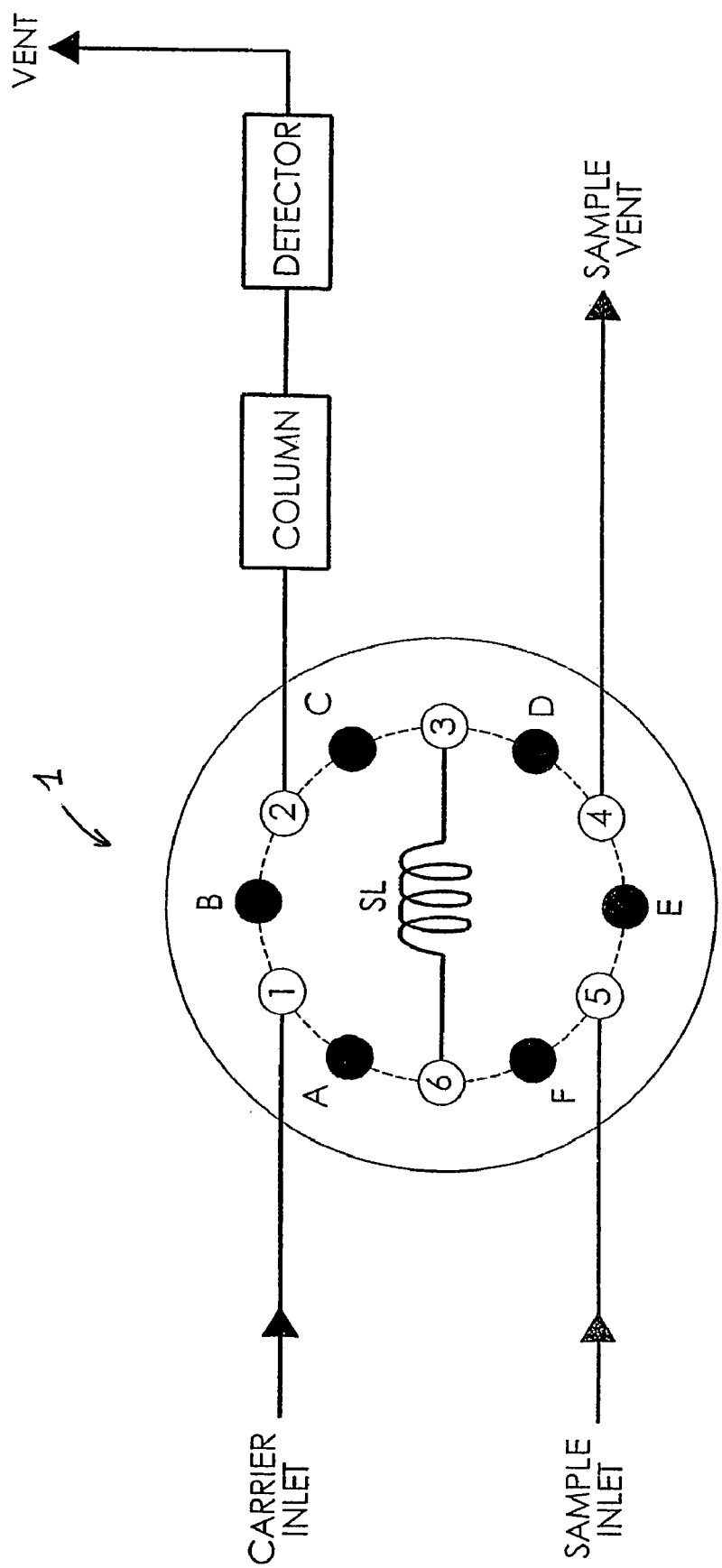
FIG. 3A (PRIOR ART) is a schematic representation of the valve shown in FIG. 2A, the valve being in an intermediate position.
Figure 3B:
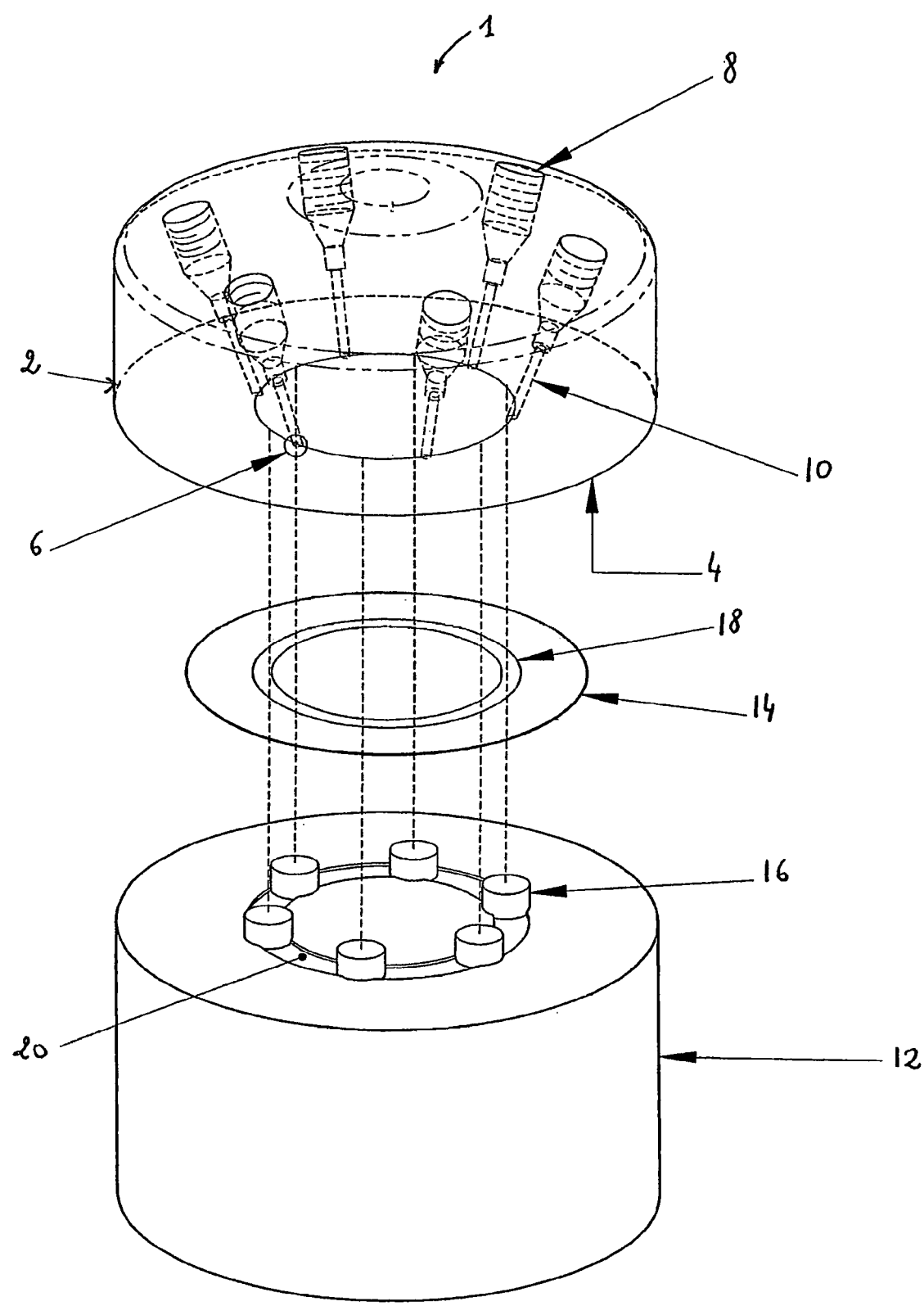
FIG. 3B (PRIOR ART) is an exploded perspective view of the valve shown in FIG. 3A.
Figure 4A:
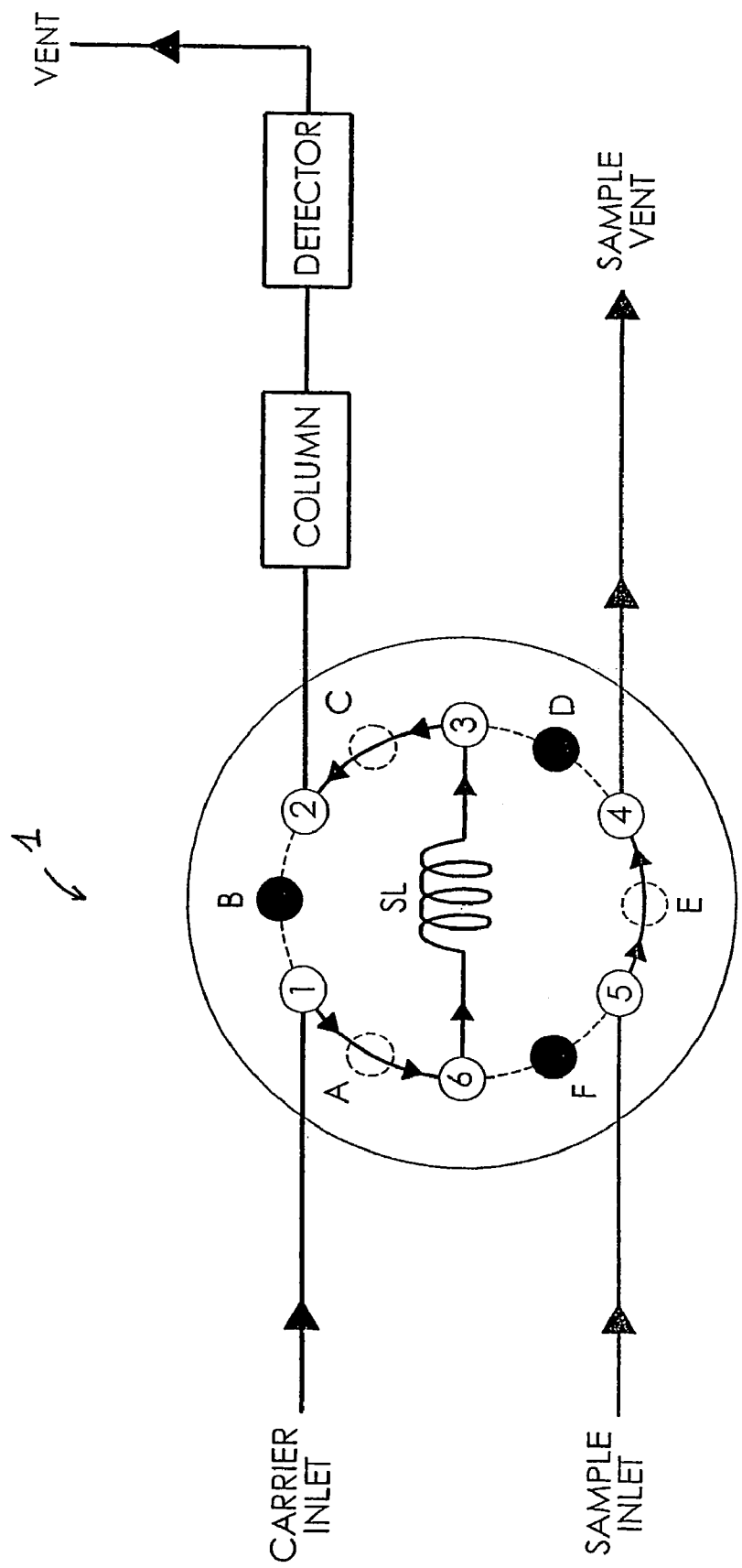
FIG. 4A (PRIOR ART) is a schematic representation of the valve of FIG. 2A, the valve being in a sample injection position.
Figure 4B:
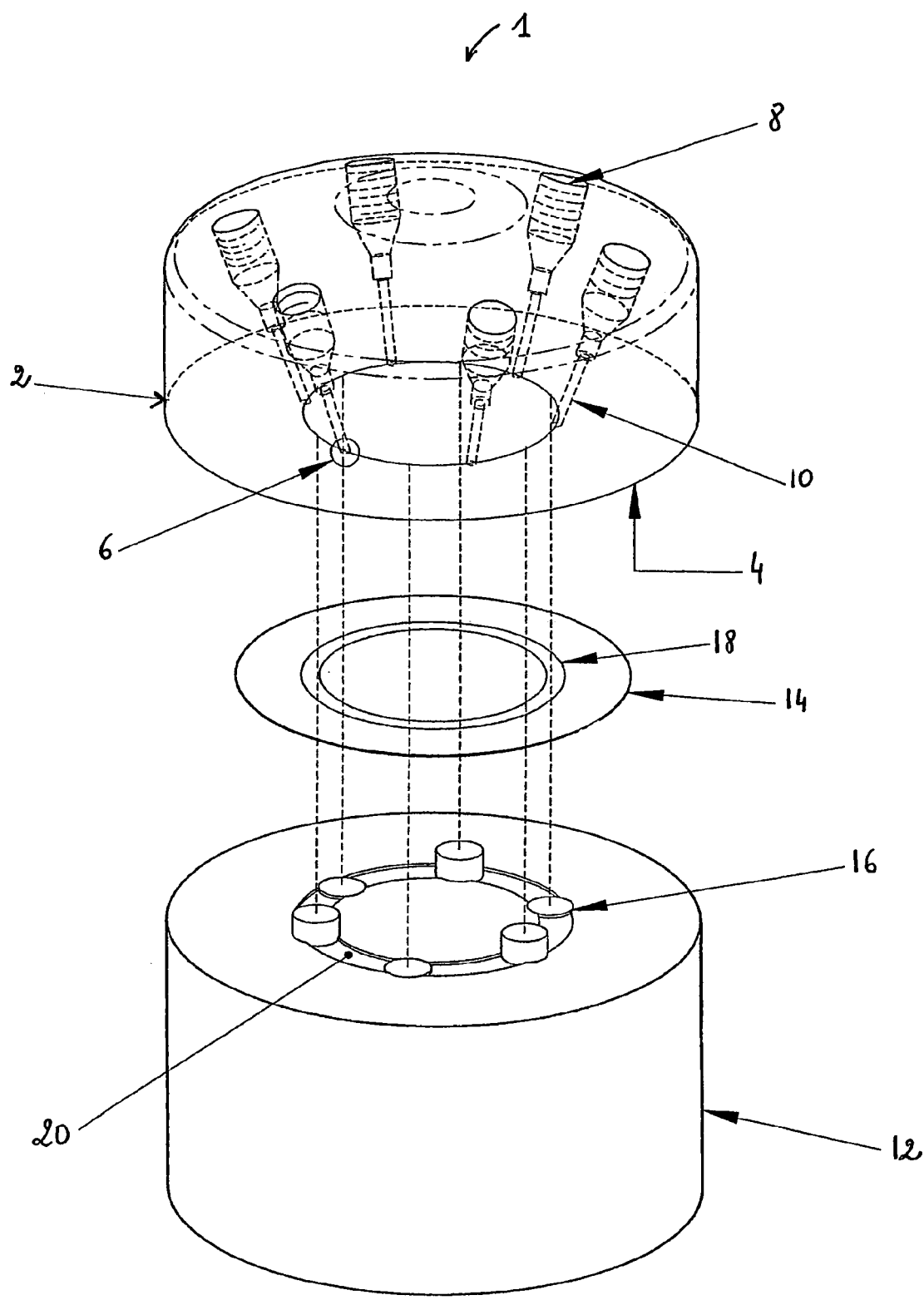
FIG. 4B (PRIOR ART) is an exploded perspective view of the valve shown in FIG. 4A.
Figure 9A:
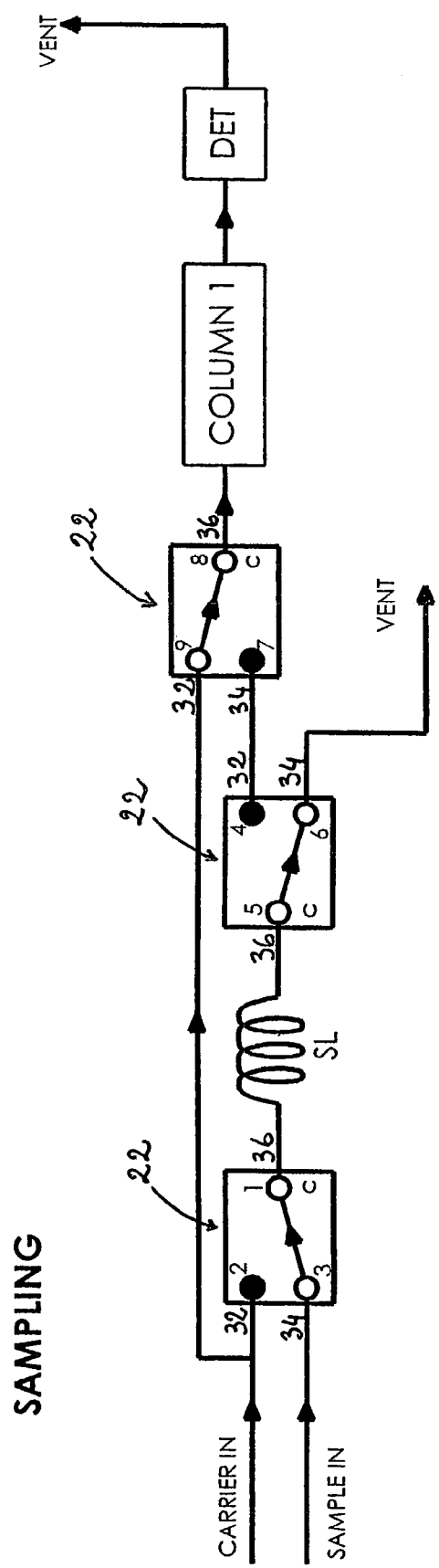
FIG. 9A is a schematic representation of a typical chromatographic application using the valve of the present invention shown in FIG. 5, the valve being in the sampling position.
Figure 9B:
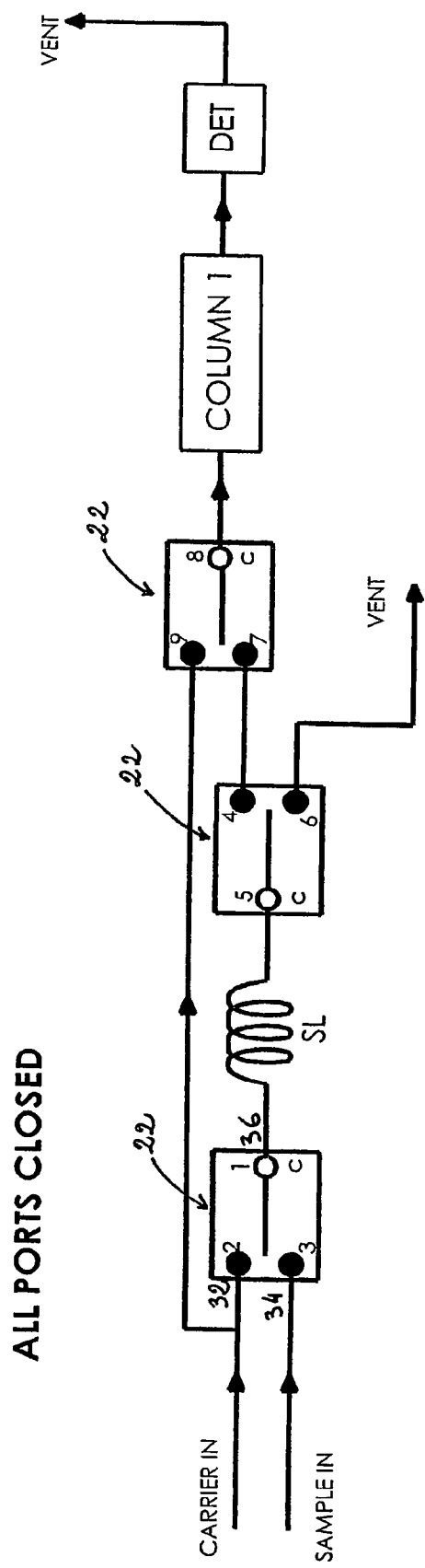
FIG. 9B is a schematic representation of the chromatographic application illustrated in FIG. 9A, the valve being in the intermediate position.
Figure 9C:
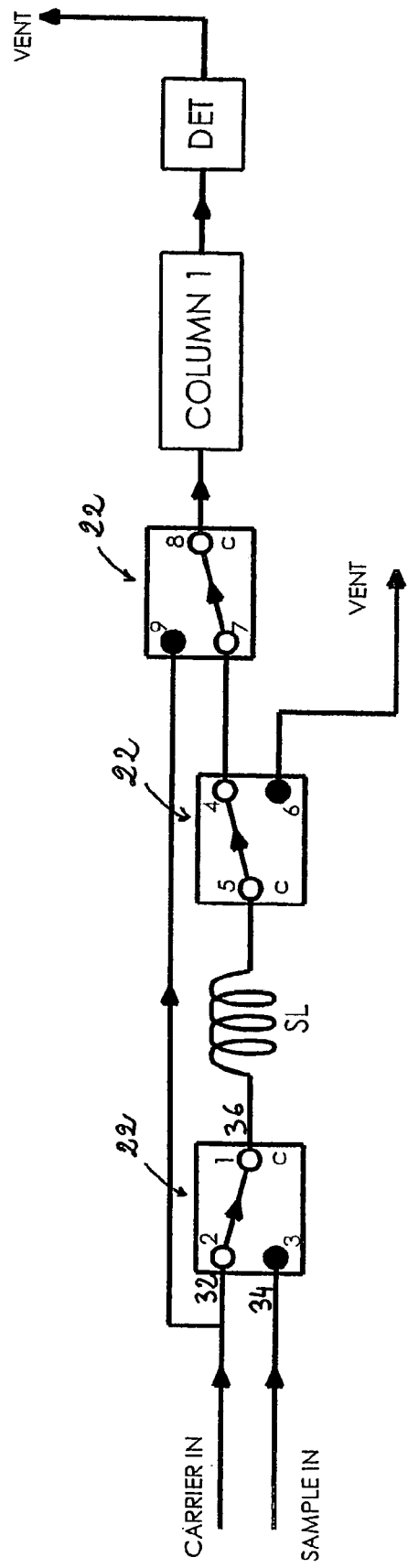
FIG. 9C is a schematic representation of the chromatographic application illustrated in FIG. 9A, the valve being in the sample injection position.

Referring again to FIG. 2A, there is shown a typical chromatographic application known in the art, which uses a six port traditional gas chromatographic valve. When the valve is actuated, the sample is injected or put into the carrier circuit as shown in FIG. 4A. FIGS. 9A to 9C show schematic representations of the different steps which could be realized with the application illustrated in FIG. 2A but realized with the valve 84 of the present invention. In this preferred embodiment of the invention, the valve 84 is provided with three elementary switching cells 22. Each switching cell 22 is represented by a rectangular box with three small circles identifying the ports. The letter c in the rectangular box identifies the common port 36. FIG. 9A shows the valve 84 at power off. This position is the sampling one like shown in FIG. 2A. FIG. 9B shows the intermediate position wherein all ports 32, 34 are closed to prevent port flow mixing, like in FIG. 3A. Finally, FIG. 9C shows the sample injection position, like in FIG. 4A.

Figure 10A:
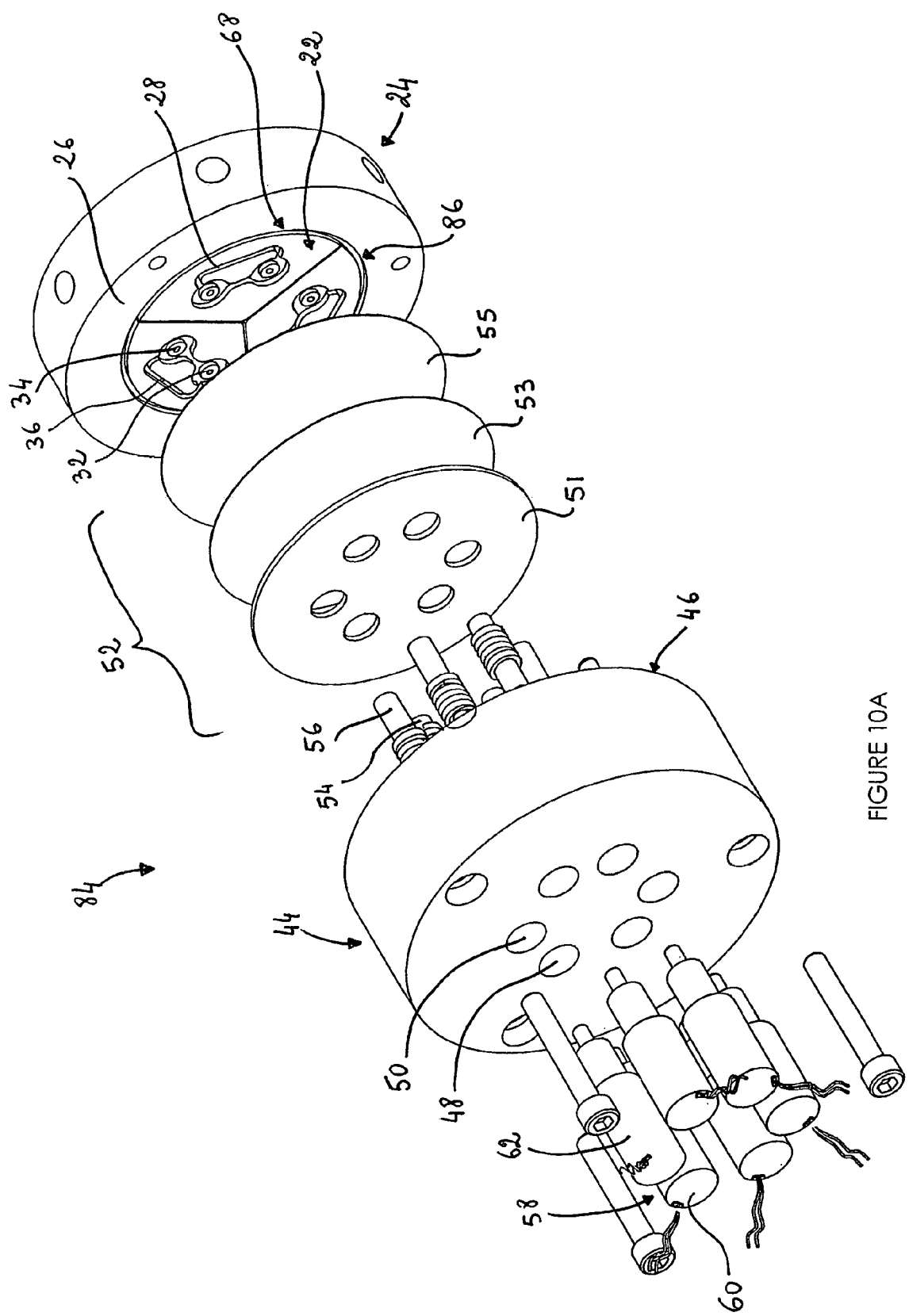
FIG. 10A is an exploded perspective view of a diaphragm-sealed valve, according to another preferred embodiment of the present invention.
Figure 10B:
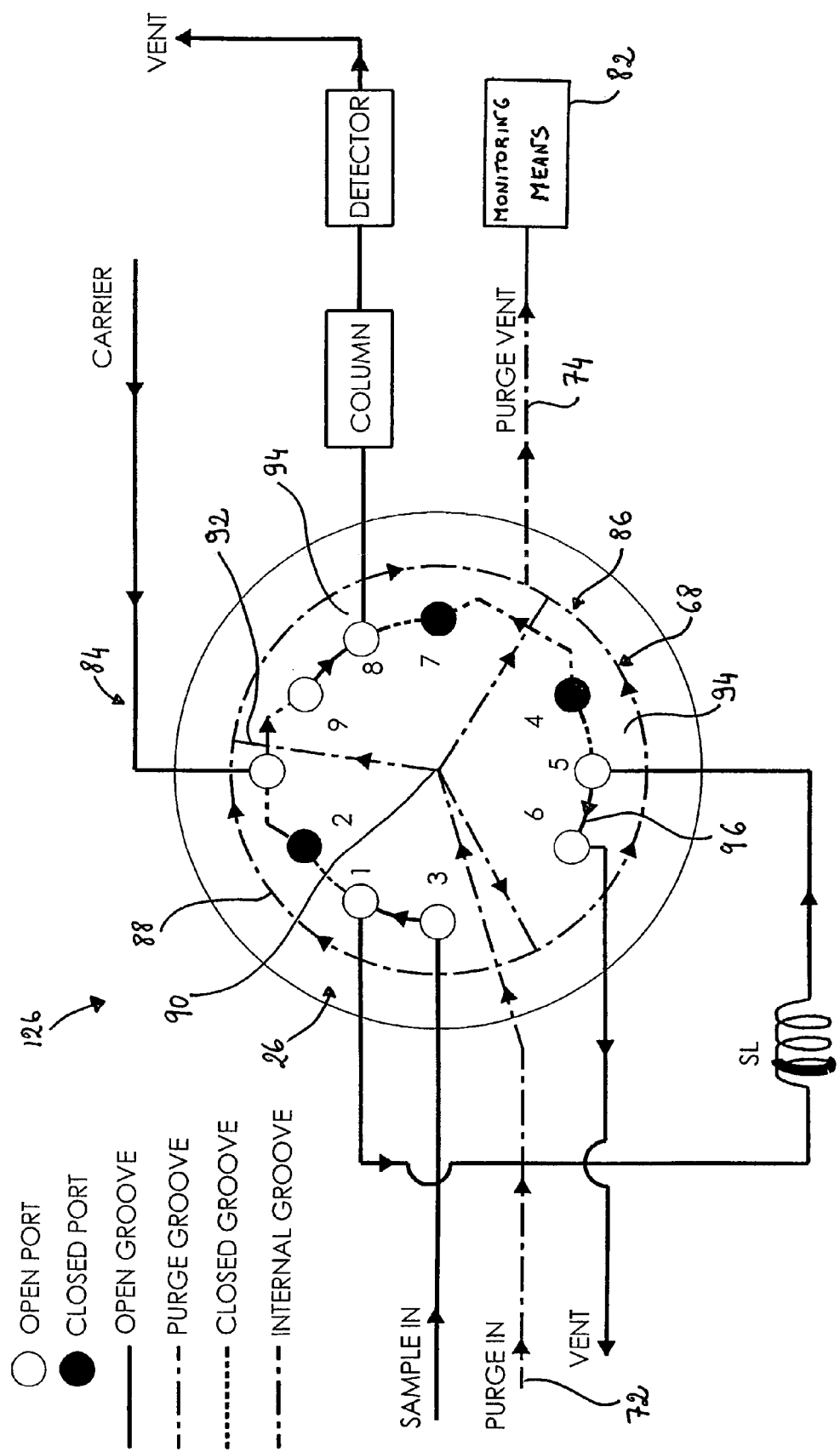
FIG. 10B is a schematic representation of the valve shown in FIG. 10A, the valve being in the sampling position.
Figure 10C:
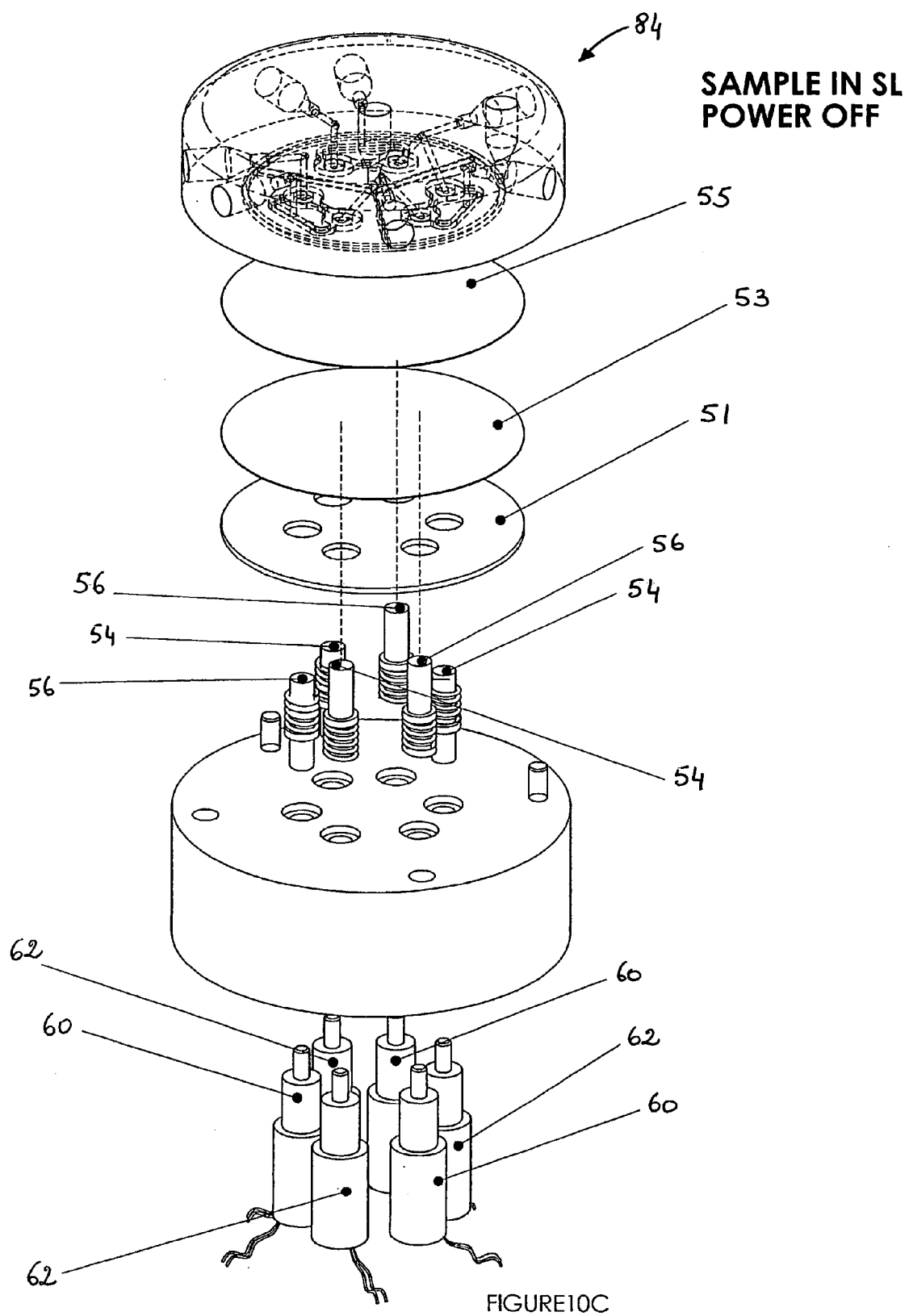
FIG. 10C is an exploded perspective view of the valve shown in FIG. 10B.
Figure 10D:
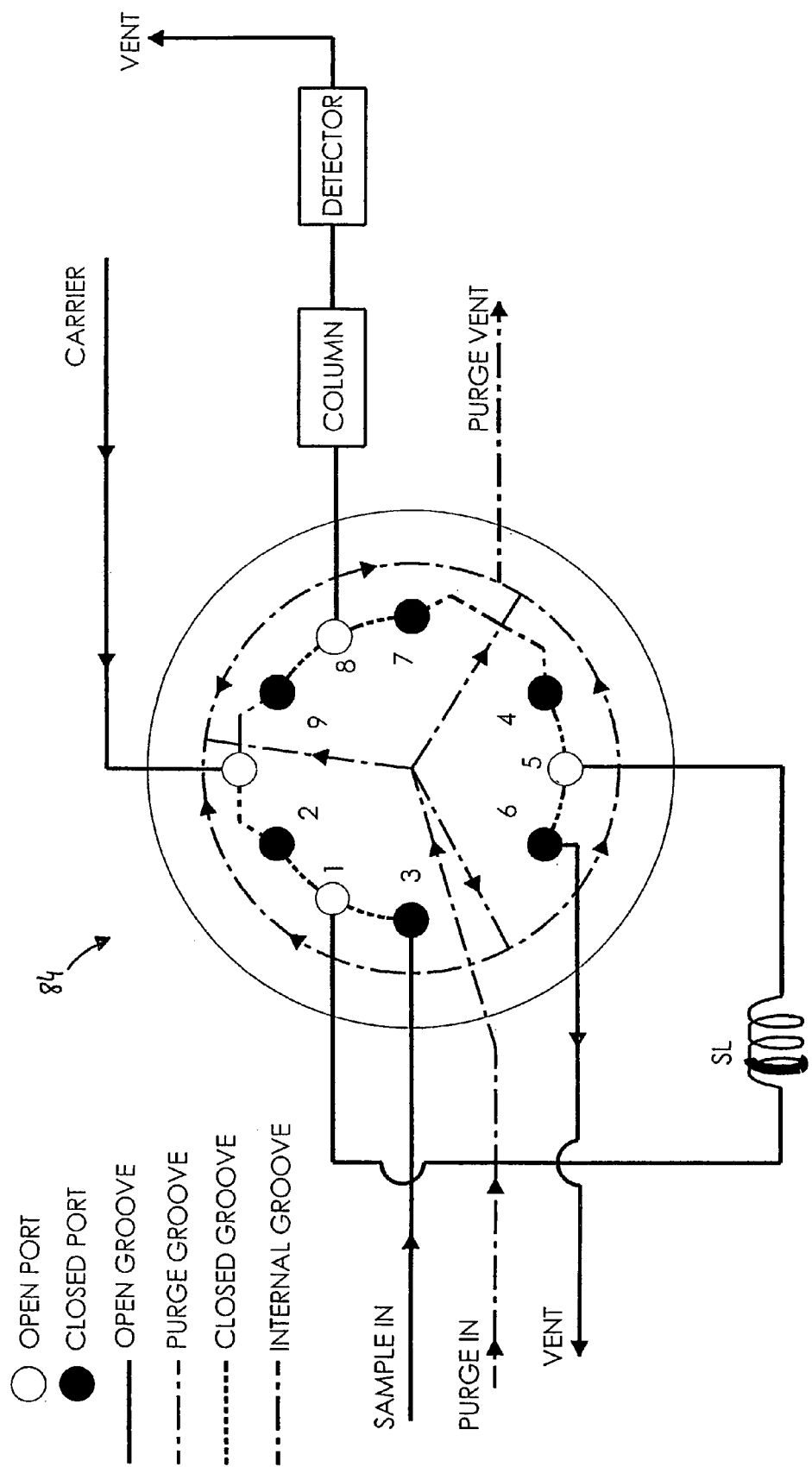
FIG. 10D is a schematic representation of the valve shown in FIG. 10A, the valve being in the intermediate position.
Figure 10E:
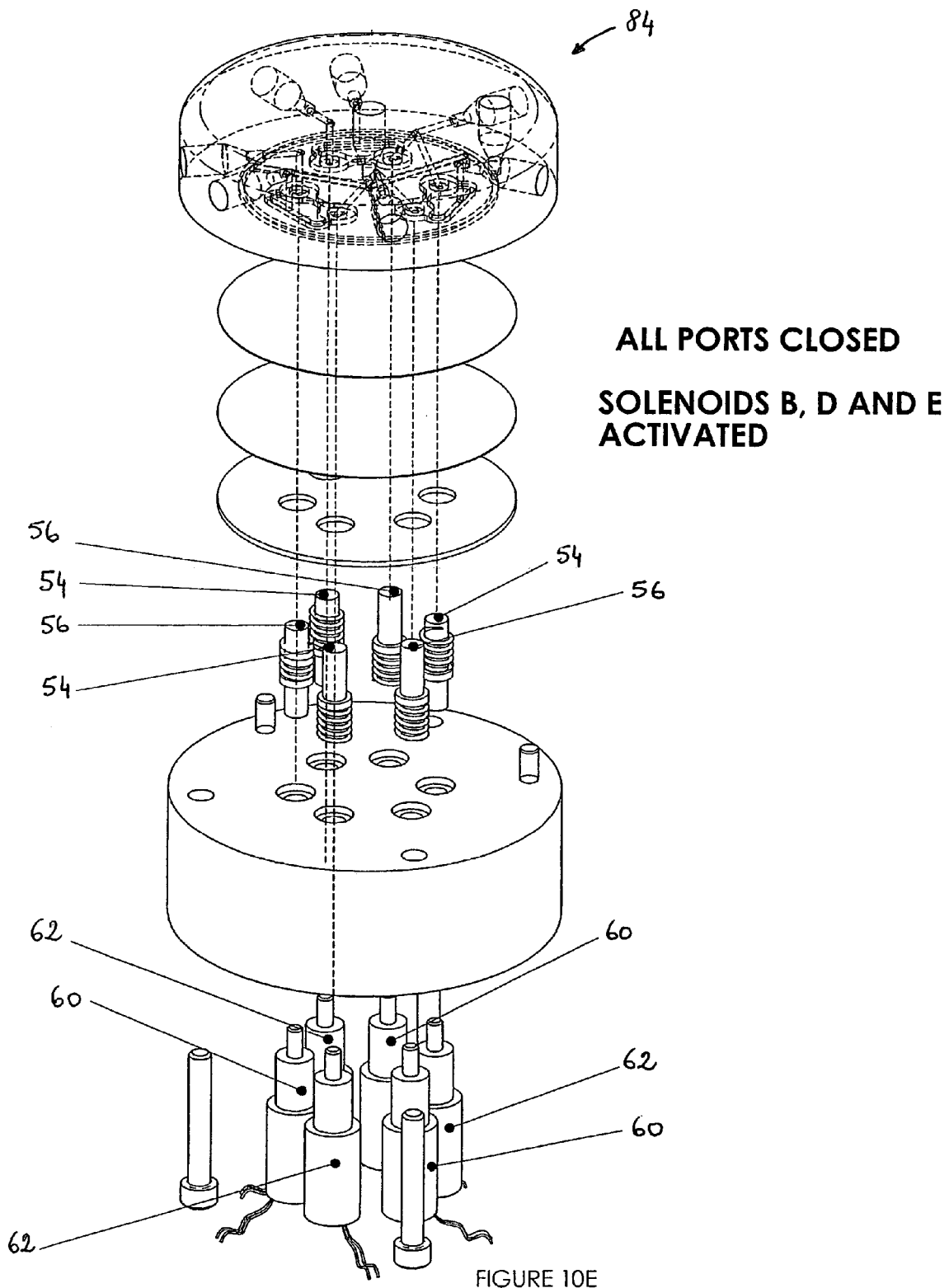
FIG. 10E is an exploded perspective view of the valve shown in FIG. 10D.
Figure 10G:
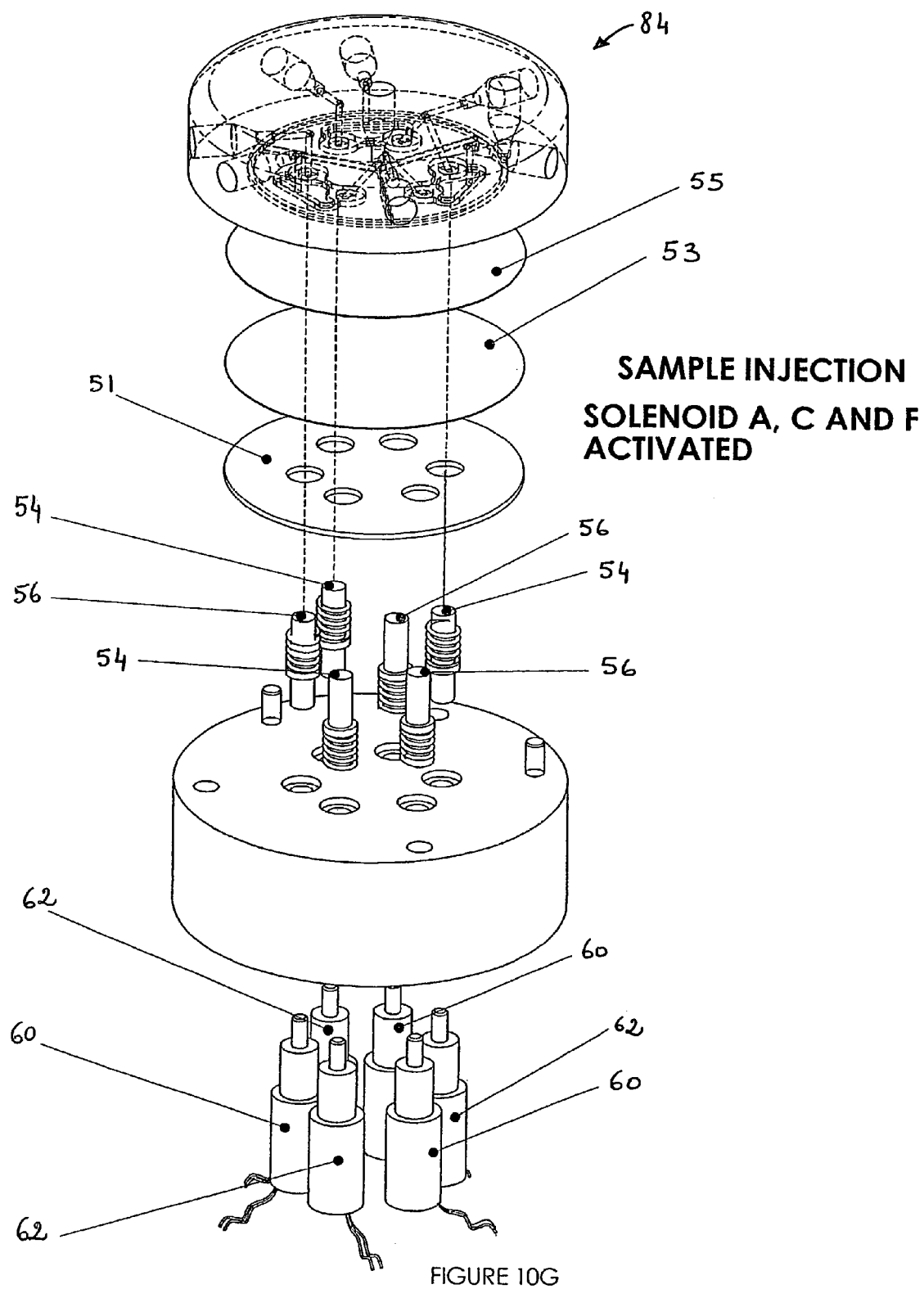
FIG. 10G is an exploded perspective view of the valve shown in FIG. 10F.

FIGS. 10A to 10G illustrate the valve 84 of the present invention in different positions. FIGS. 10B and 10C show the sampling mode position, FIGS. 10D and 10E show the intermediate position wherein all ports 32, 34 are closed, while FIGS. 10F and 10G show the sample injection position. So, one can see that the three elementary switching cells 22 are simply embedded in the same substrate. As described above, in this illustrated preferred embodiment, there is an outer annular recess 88 surrounding all of the cells 22, and separation recesses 92 for isolating each of the cells 22. Thus, a purging fluid can advantageously be introduced into the fluid inlet 72, preferably extending in the inner recess 90, where the separation recesses 92 join together. This purging fluid can thus flow through the separation recesses 92 between the cells 22, and then to the outer annular recess 88 and then exit by the fluid outlet 74, preferably extending therein. Of course, the fluid inlet 72 could extend in the outer recess 88 while the fluid outlet 74 could extend in the inner recess 90. So any leak that may occur over the time from anyone of the cells 22 will reach the purge circulation line 68 first, avoiding contaminating the other cells. Indeed, with reference to FIG. 10B, the valve 84 can advantageously be used in an analytical chromatographic system 126 to provide a system having improved characteristics. Such an analytical chromatographic system 126 is advantageously provided with a diaphragm-sealed valve 84 having a purge circulation line 68 as described above. The analytical system 126 is also advantageously provided with monitoring means 82 operatively connected to the fluid outlet 74 for monitoring a fluid passing therethrough. In a preferred embodiment, the monitoring means 82 have a purity detector for detecting contamination of said fluid. Preferably, the monitoring means 82 are adapted to monitor the fluid passing through the purge circulation line 68 continuously. Again, this feature is well explained in our previous US application. In this illustrated valve configuration, one of the switchable ports 32, 34 is preferably closed while the other switchable port 32 or 34 is opened when the valve is at rest or not actuated. Again, the springs 64, 66 associated to the plungers 54, 56 are advantageously particularly arranged to push down one plunger and move up the other one. Each of the three cells 22 is configured this way. It is an advantageous convenient way to provide all the switching cells 22 on the same substrate, since it eliminates tubing connections. The ports connected together are preferably linked by an internal conduct drilled in the substrate. It is also possible to use three elementary separate cells 22 and connect them together with tubing. The result would be the same and there would be no difference on performance.

The valve design provided by the present invention resolves another problem inherent to the design of the prior art valves. Indeed, in the prior art, when a valve is operated to inject a sample, the cycle is generally done in three steps: sampling, isolating (all ports closed) and finally the sample injection. In gas chromatography, most of the time the sample is at ambient or sub atmospheric pressure and the carrier is at much higher pressure. Since the sample is at low pressure, the sample volume of the sample loop is made bigger to have more sample, and then more impurities, in order to increase the sensitivity of the gas chromatographic system. Mostly, in the prior art, the sample loop is generally made of tubing having a diameter bigger than the tubing of the gas chromatographic carrier circuit. For example, it is not uncommon to have a sampling loop having an outer diameter of ⅛", while the carrier distribution network is made of tubing having an outer diameter of 1/16". So, when suddenly the sample volume is introduced into the carrier circuit, there is a system flow and pressure perturbation. When the system sensitivity is high, this perturbation generally generates a dramatic detector's baseline shift that interferes with the impurities to be measured, thereby reducing the overall system repeatability and sensitivity. The impact is even more dramatic in a system wherein a permeation tube or a dopant gas are added to the detector, since flow variation results in change of dilution ratio, thereby changing the level of dopant into the detector. Moreover, the pressure or flow variation can also change the separation column operating conditions. Indeed, since the sample loop must be pressurized before the flow comes back to its operating point, the column inlet pressure decreases and there is a reverse flow from the column. In gas solid chromatography, the column packing may eventually release some molecules that are normally trapped into the column. When the flow starts back, a part of these molecules will reach the detector, thereby generating a false peak or baseline shift.

Figure 11:
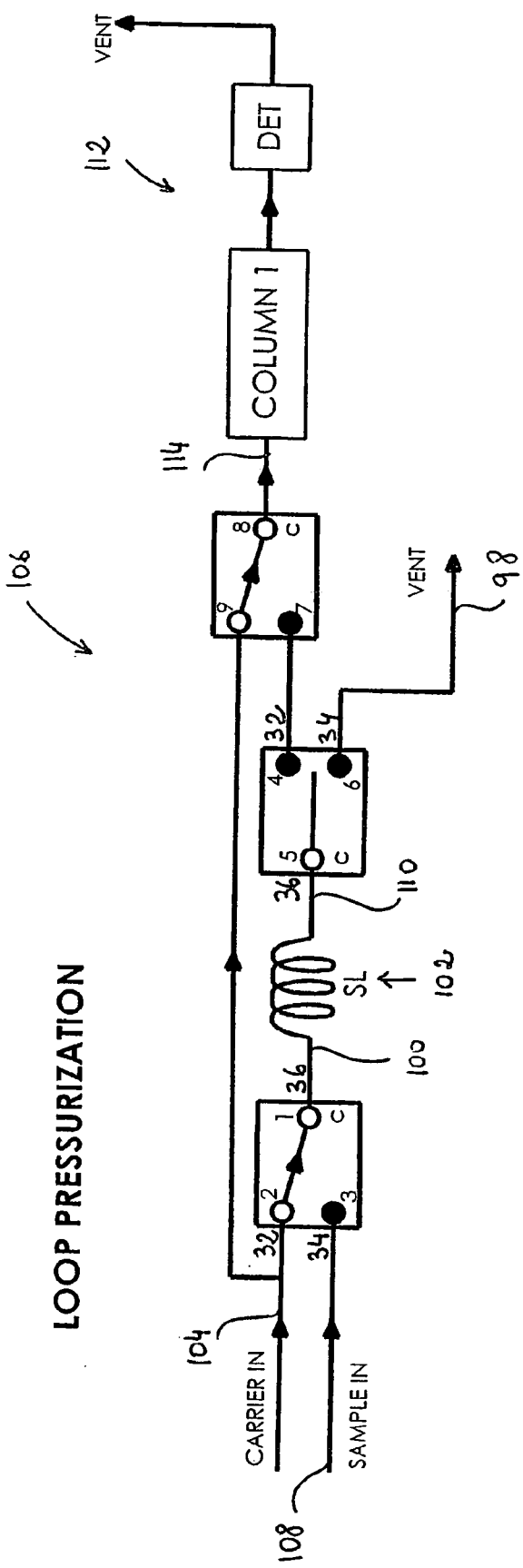
FIG. 11 is a schematic representation of an analytical chromatographic method, according to a preferred embodiment of the present invention.
Figure 12A:
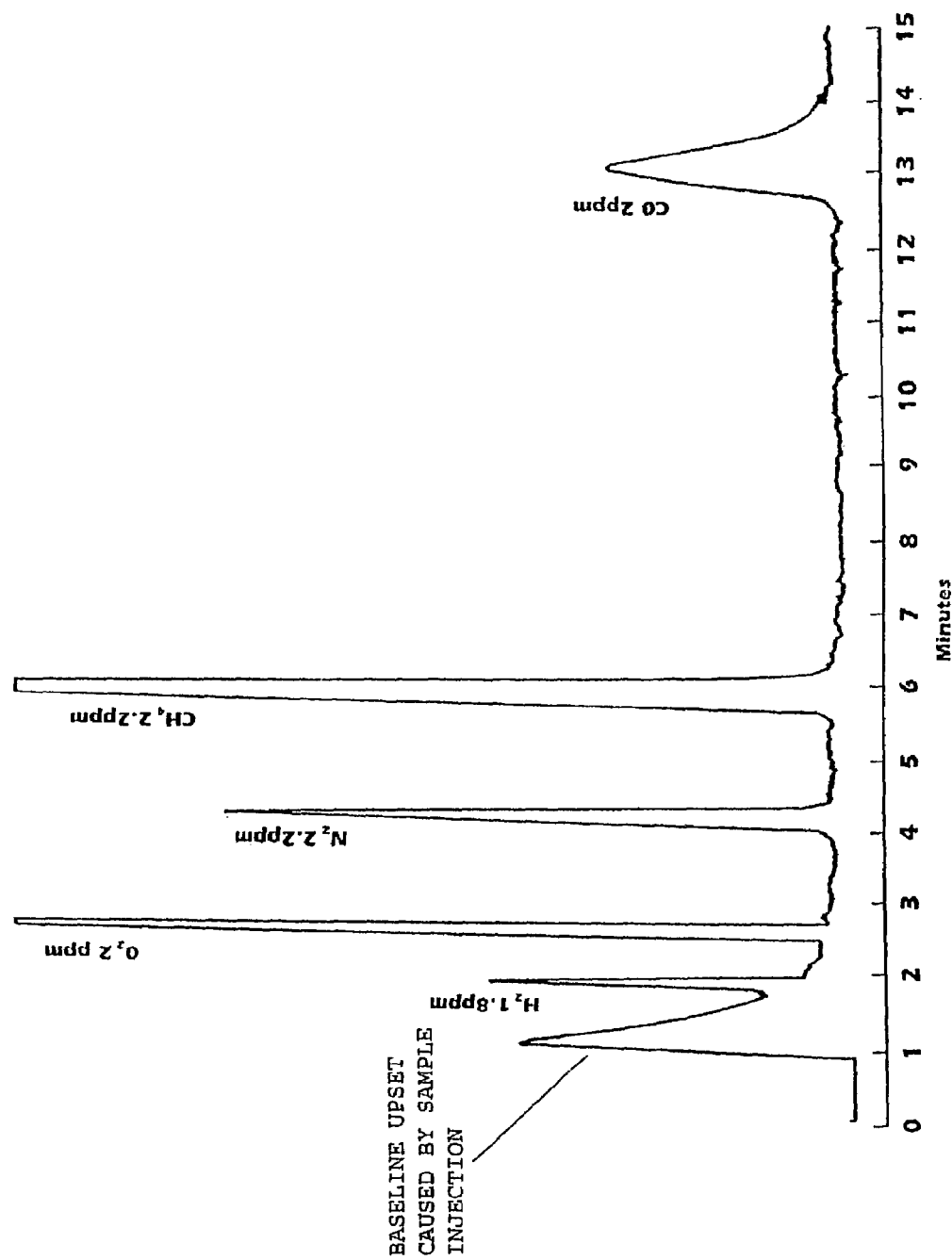
FIG. 12A illustrates a conventional baseline generated by a prior art valve.
Figure 12B:
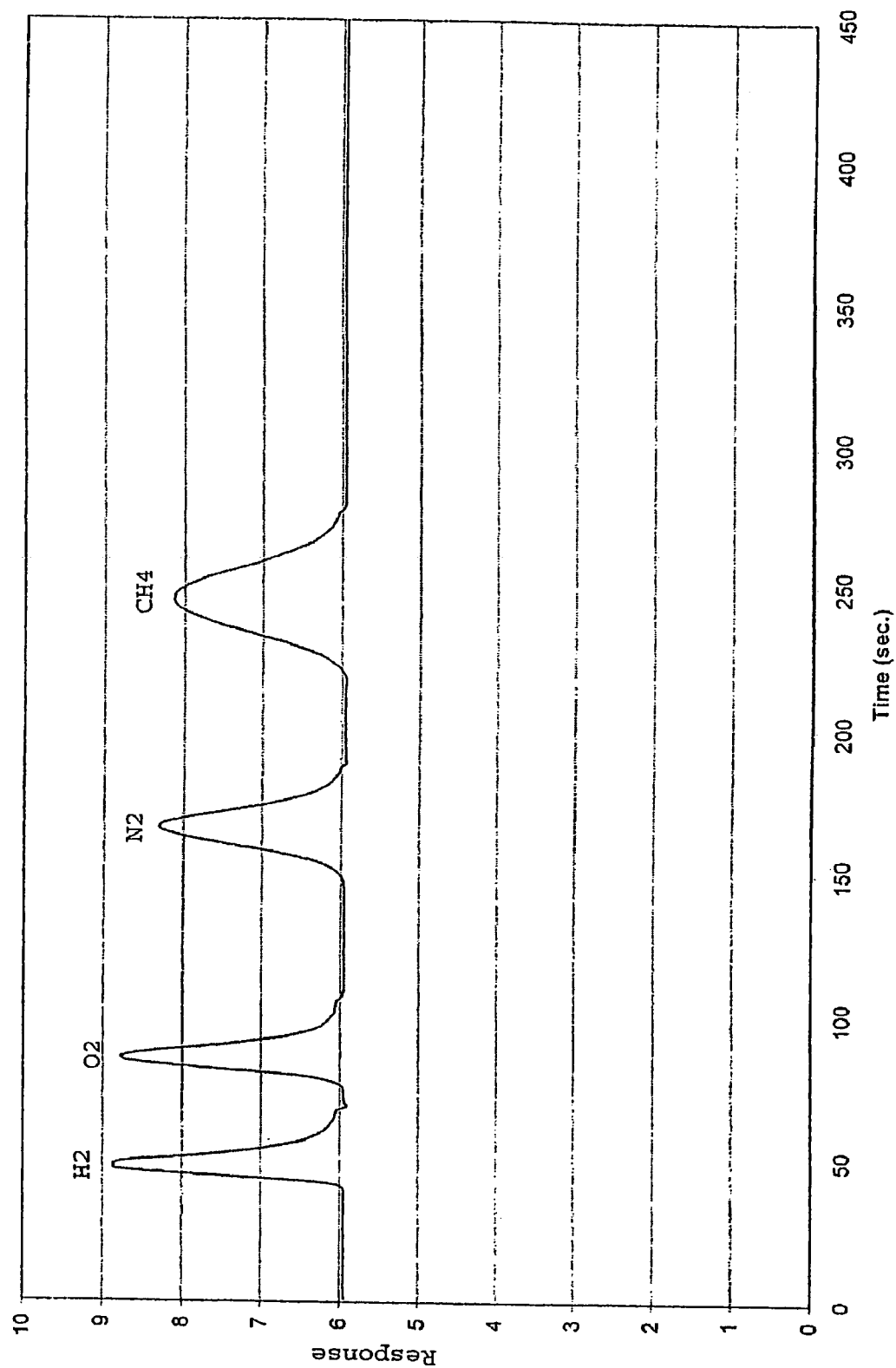
FIG. 12B illustrates a baseline generated by a preferred embodiment of the valve of the present invention.

However, with the diaphragm sealed valve provided by the present invention, most of these prior art drawbacks can be overcame. Indeed, with the valve of the present invention, another step may be added to a conventional injection cycle. The cycle is then: sampling, sample loop isolation and pressurization, all ports closed and sample injection. The sample loop isolation and pressurization step is shown in FIG. 11. In this step, the vent side 98 of the sampling loop 102 is closed by actuating the associated solenoid. The inlet 100 of the sampling loop 102 is then connected to the carrier inlet 104, as shown by the valve flow path. In this position, the sampling loop 102 is pressurized at a pressure equal to the column head pressure. At this moment, the sampling loop 102 is put into the carrier circuit. There is no perturbation generated. FIG. 12A shows a conventional baseline where a sample is injected with a conventional valve. One can see there is a strong upset. In FIG. 12B, the conventional valve has been replaced with the valve of the present invention. One can see that no upset occurs, even when enlarging the baseline. This method has a beneficial impact on hardware used to regulate carrier flow and pressure since there is no more column head pressure variation. Thus, a simpler regulation method can be used instead of those of the prior art, thereby allowing to reduce the overall system cost and complexity.

Accordingly, still with reference to FIG. 11, the present invention thus provides an improved analytical chromatographic method. This improved method comprises the steps of:

a) providing a fluid sampling system 106 comprising a diaphragm-sealed valve 84 provided with a plurality of independently actuated ports 32, 34 serially interconnected to each other. The fluid sampling system 106 further has a sample inlet 108, a carrier inlet 104, a sampling loop 102 having an inlet 100 and an outlet 110, a sample vent line 98 and analytical means 112 provided with an inlet 114, each being operatively interconnected to the valve 84 through a corresponding one of the ports;

b) providing fluid communication from the sample inlet 108 to the inlet 100 of the sampling loop 102 by actuating the corresponding ports 32, 34, thereby providing a fluid sample in the sampling loop 102;

c) closing the outlet 110 of the sampling loop 102 by actuating the corresponding port 32, 34 to isolate the sampling loop 102;

d) providing fluid communication from the carrier inlet 104 to the inlet 100 of the sampling loop 102 by actuating the corresponding port 32, 34 to pressurize the sampling loop 102;

e) preventing fluid communication from each of the ports 32, 34, 36 to the remaining ports by actuating the corresponding ports; and f) providing fluid communication from the outlet 110 of the sampling loop 102 to the inlet 114 of the analytical means 112 by actuating the corresponding port, thereby injecting the sample in the analytical means 112.

In the past, many have designed complex flow or pressure regulation sub-systems in the attempt of reducing baseline upset at sample injection. For example, U.S. Pat. Nos. 4,976,750 and 5,952,556 illustrate such regulation sub-systems. This goal is easily achieved with the present valve design because of the independent port actuation and positive sealing action making a leak tight system when in closed position. Moreover, with the present design, no dead volume effect occurs where part of sample can be trapped and slowly diffused back on injection and cause tailing peak.

Figure 13:
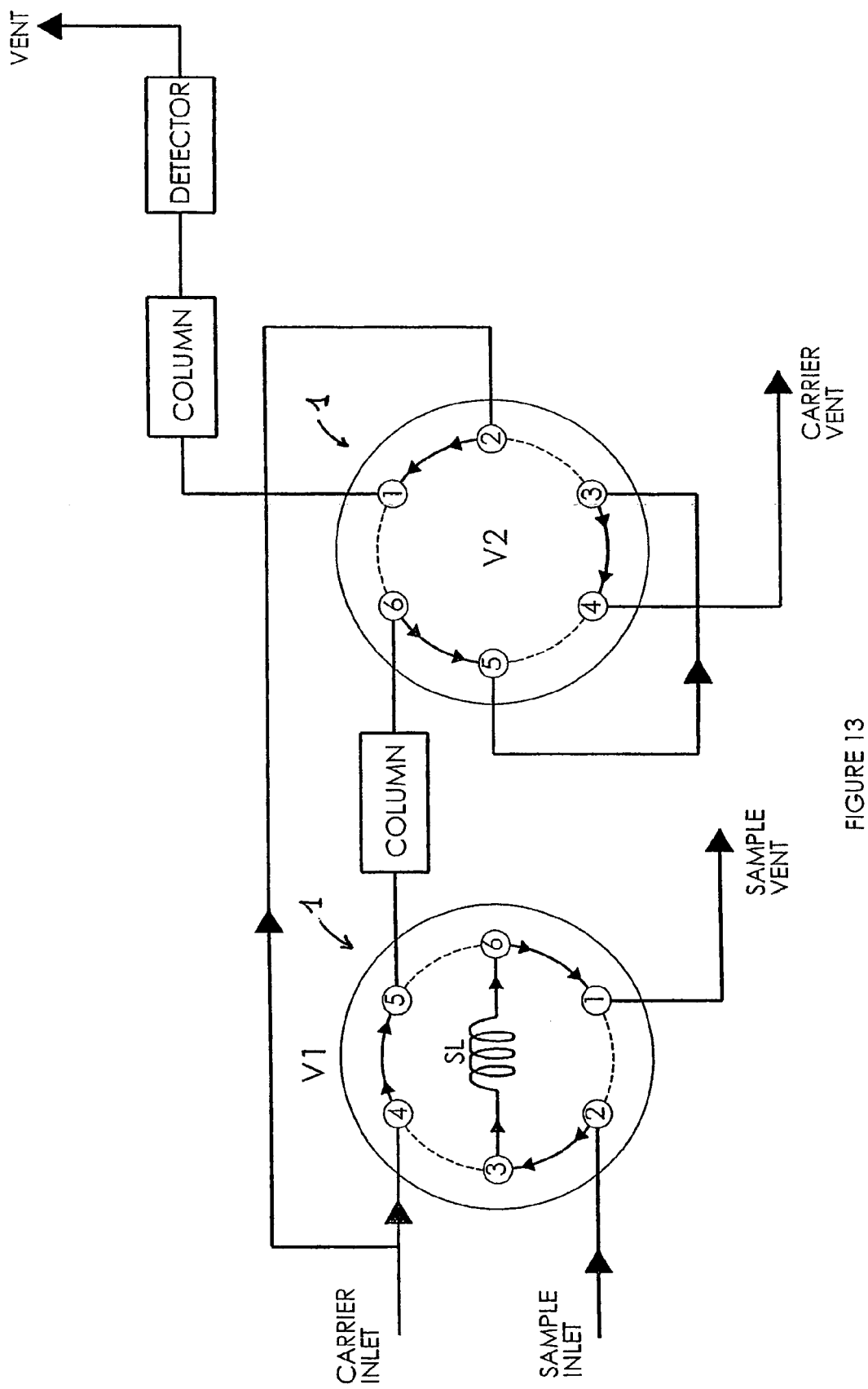
FIG. 13 is a schematic representation of another typical chromatographic application known in the art, the configuration using two six-port valves of the prior art.
Figure 14A:
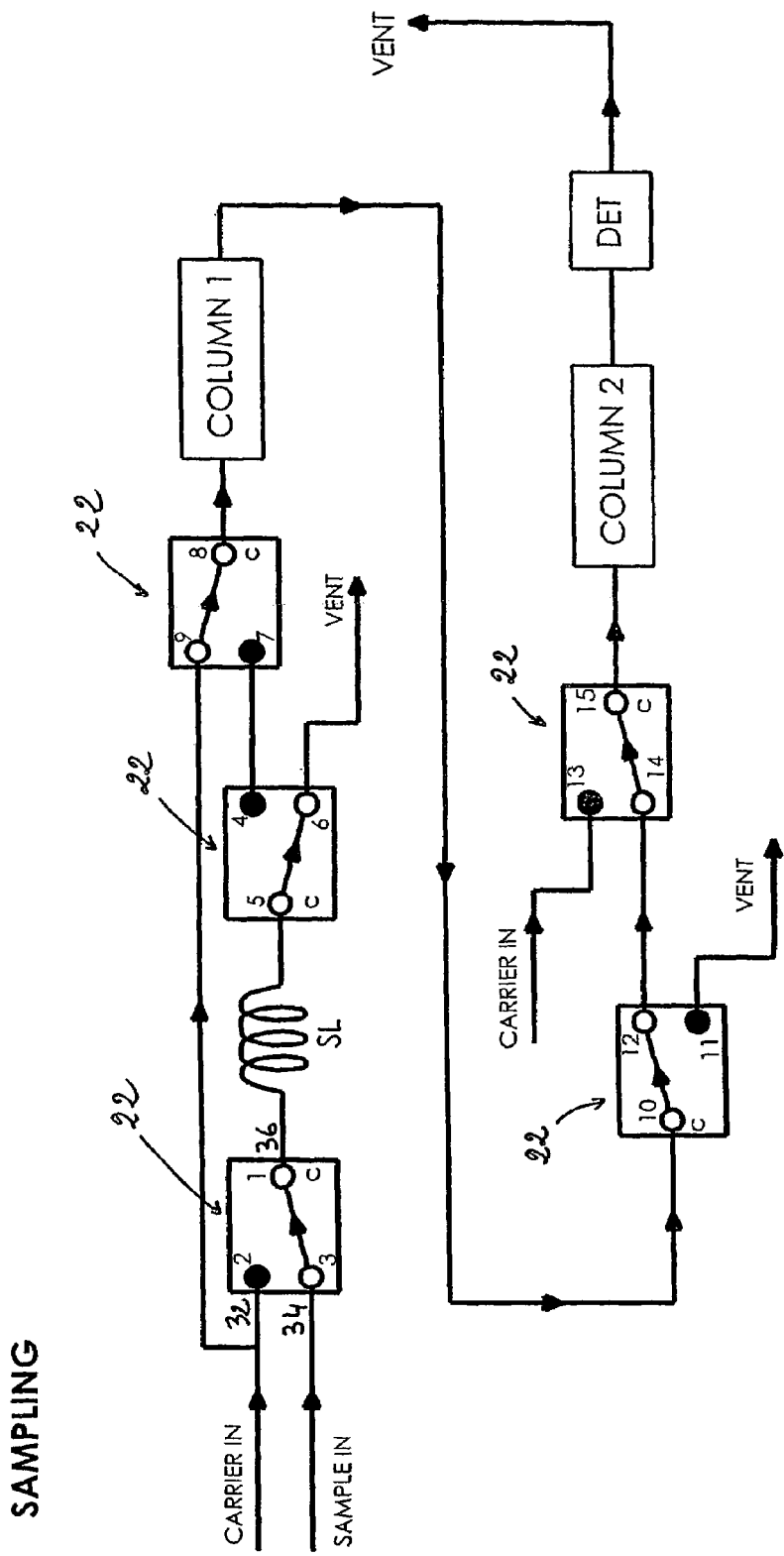
FIG. 14A is a schematic representation of the chromatographic application shown in FIG. 13, the configuration using a diaphragm-sealed valve of the present invention, the valve being in the sampling position.
Figure 14B:
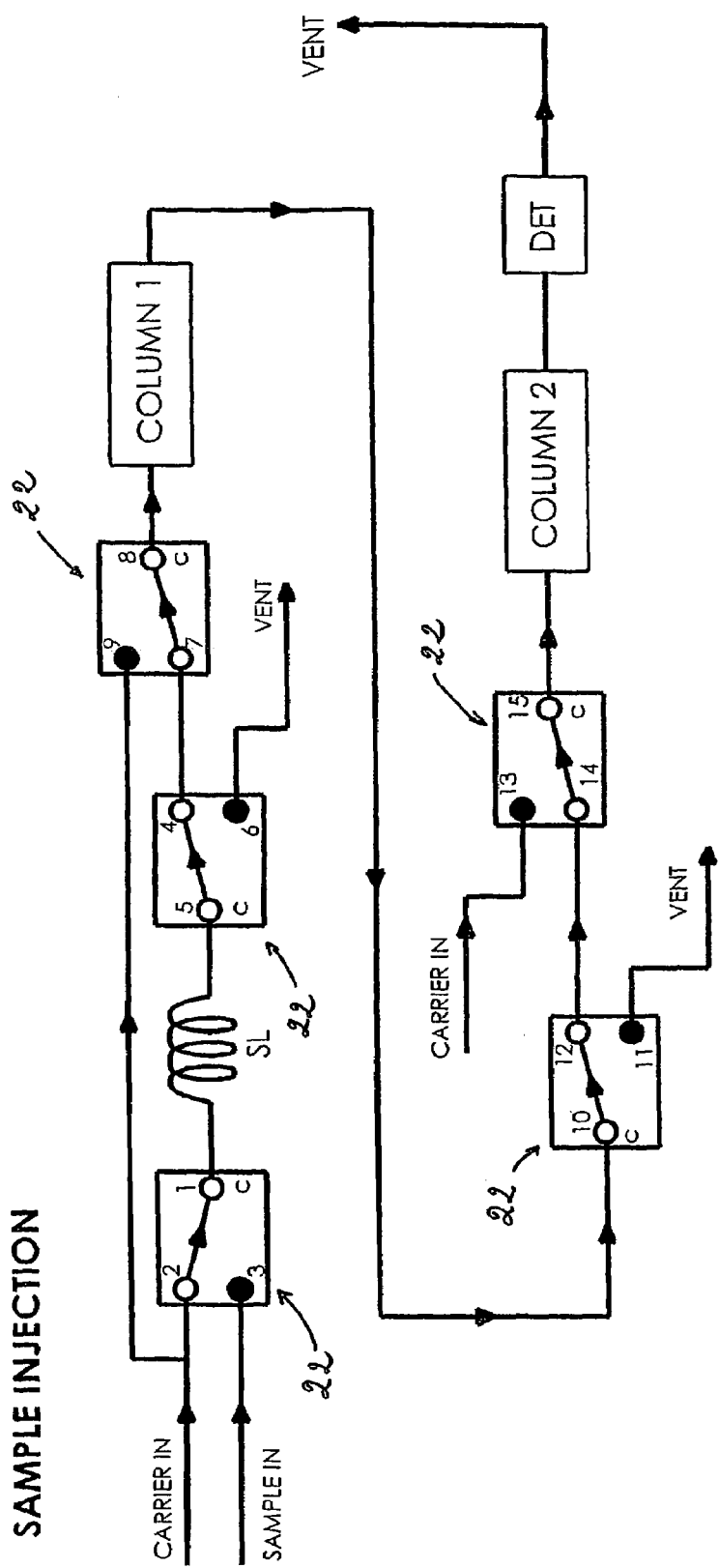
FIG. 14B is a schematic representation of the chromatographic application shown in FIG. 14A, the valve being in the sample injection position.
Figure 14C:
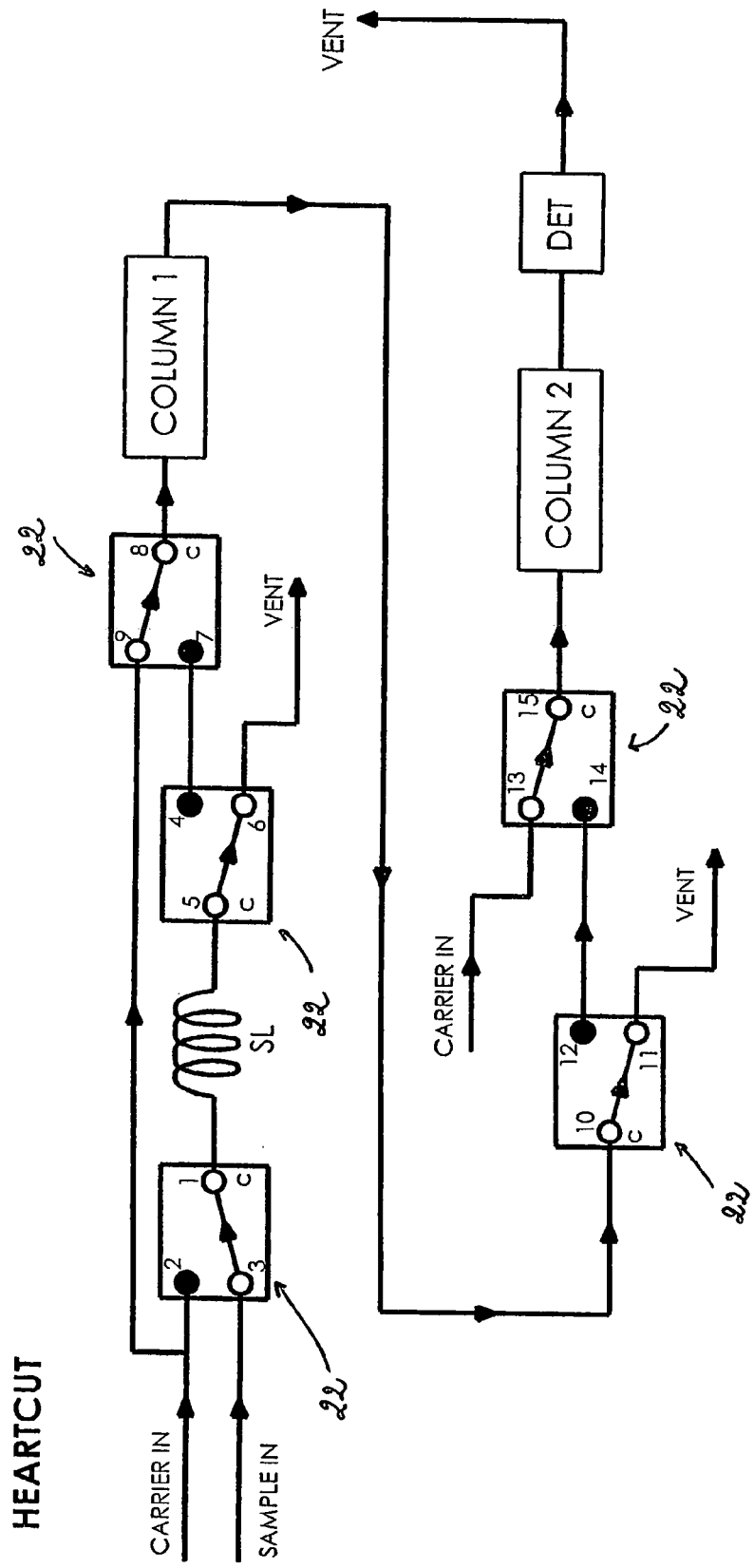
FIG. 14C is schematic representation of the chromatographic application shown in FIG. 14A, the valve being in the heartcut position.
Figure 15A:
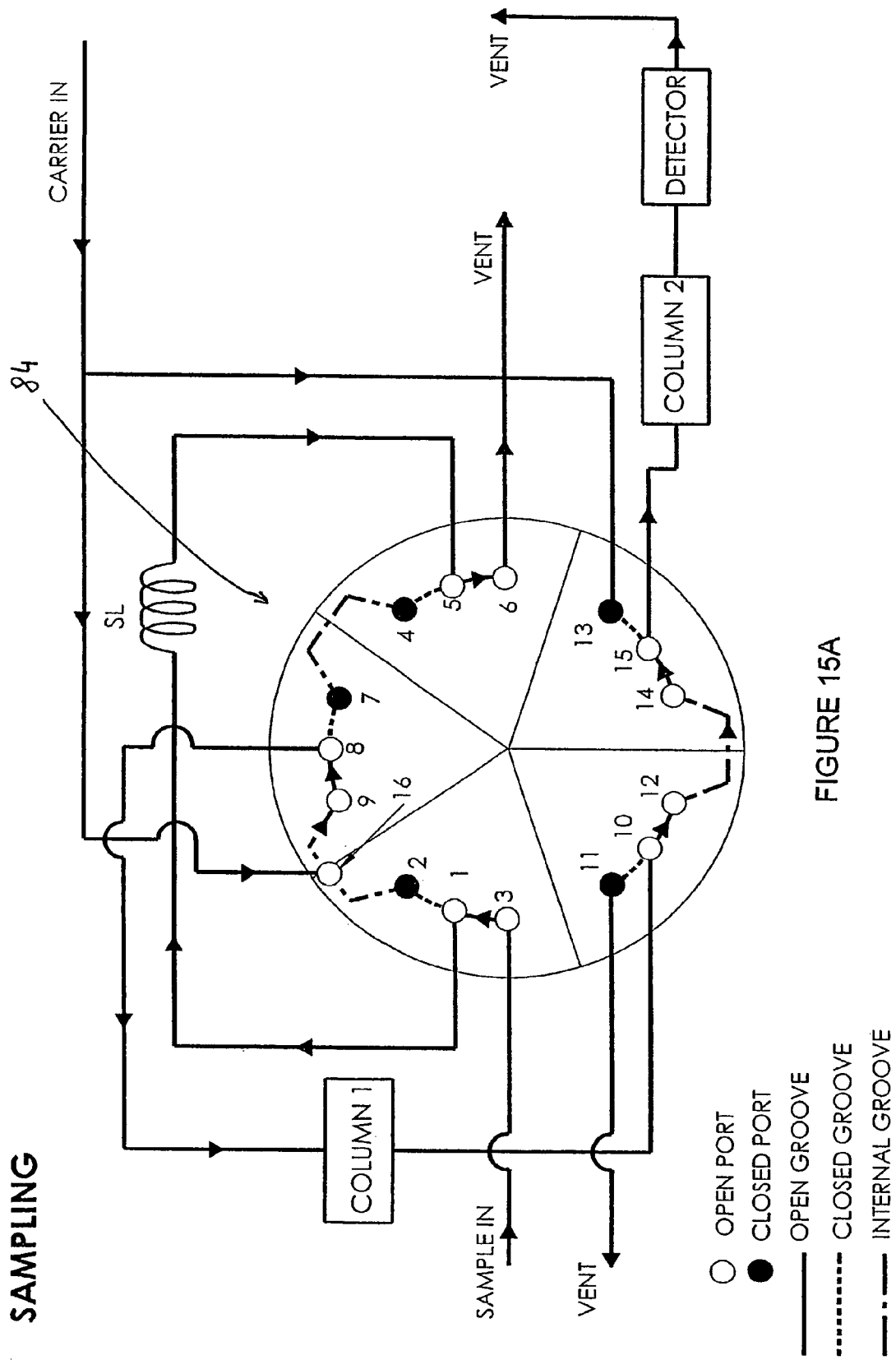
FIG. 15A is another schematic representation of the chromatographic application shown in FIG. 14A.
Figure 15B:
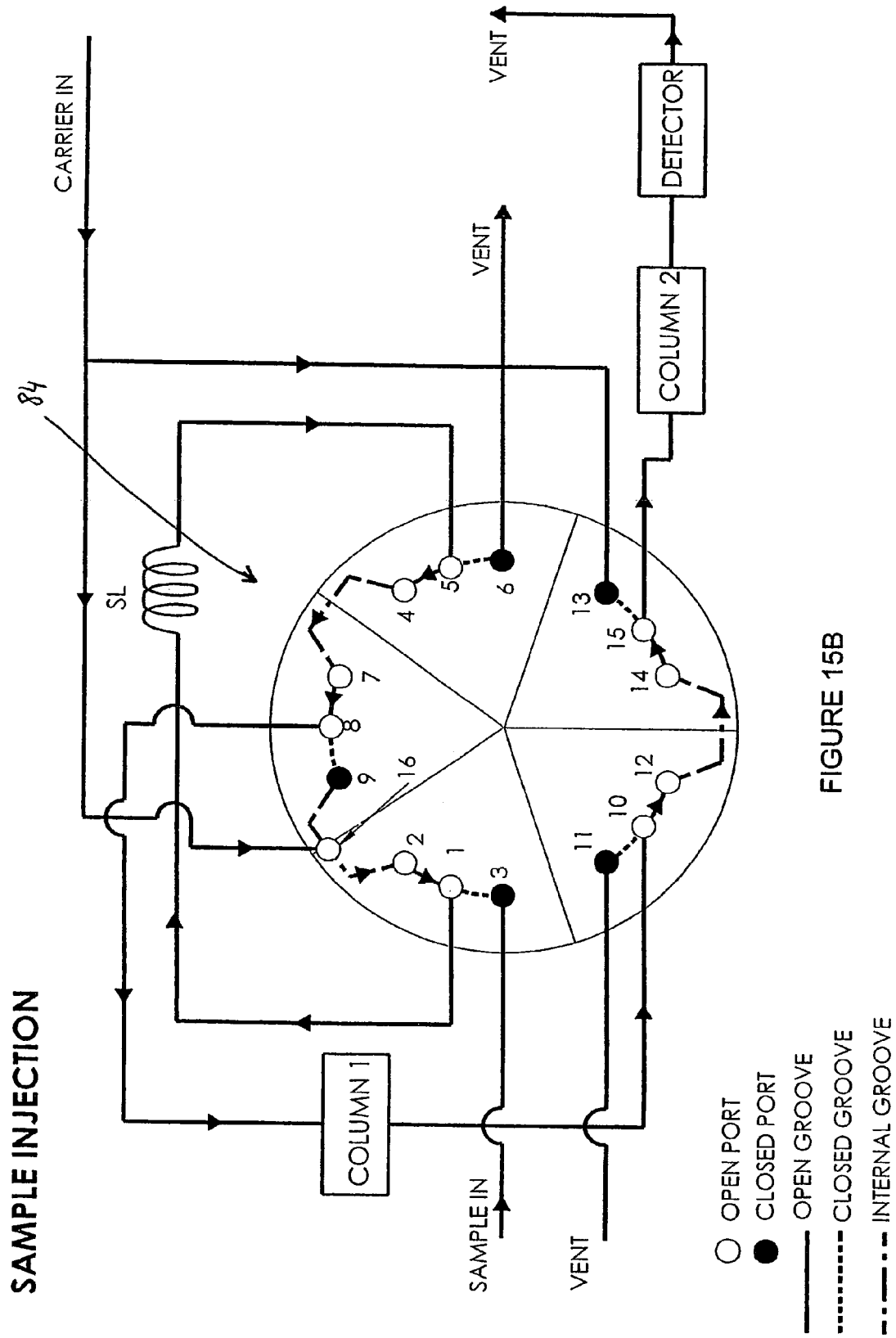
FIG. 15B is another schematic representation of the chromatographic application shown in FIG. 14B.
Figure 15C:
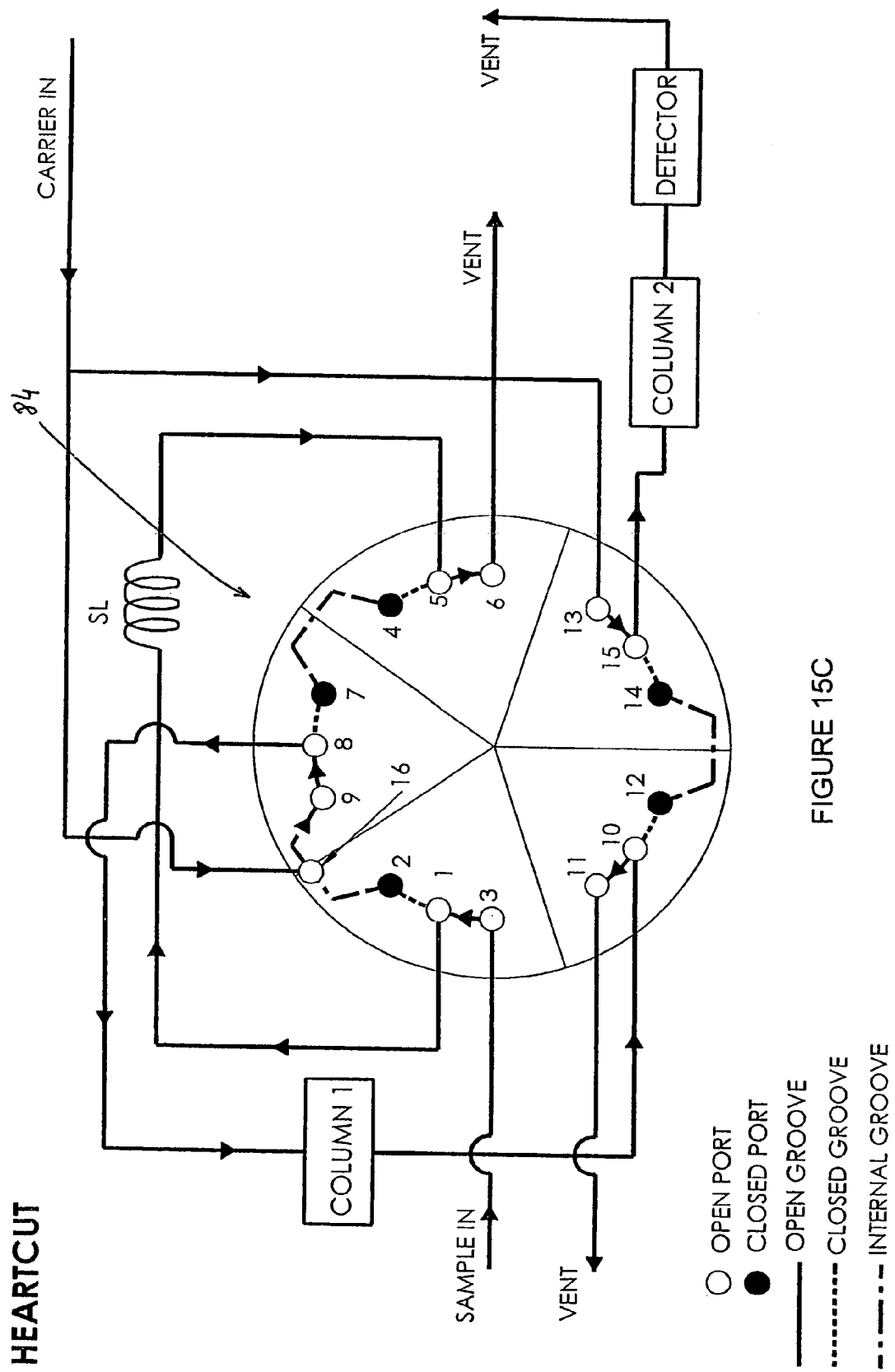
FIG. 15C is another schematic representation of the chromatographic application shown in FIG. 14C.

According to the present invention, the principle of the present valve could also be used in other typical columns, complex valves and detector configurations commonly used in the field. For example, common conventional configurations like heartcut, back flush, column selection, series-across the detector (SAD), series by-pass, trap selection, etc can be realized. So, the invention is not limited to sample loop injection. For example, a common application is the heartcut one as shown in FIG. 13. This application can be done with a 10 port valve or two six port valves. The application shown in FIG. 13 uses two six port valves of the prior art. In FIGS. 14A to 14C, this application, which is functionally equivalent to the one shown in FIG. 13, is illustrated with a plurality of three way elementary cells 22 of the present invention, in the different valve positions. FIGS. 15A to 15C show another preferred embodiment of this application using the valve 84 of the present invention, in different valve positions. The extra switching cells 22 are added to the common substrate. The switching cell ports that are common together are internally connected by flow passage machined into the first body 24 of the valve 84, thereby reducing the number of external fittings.

Another benefit of the present invention is the ease of designing complex system configurations. The fact of using only one switching cell 22 at a time allows to more easily design multiple columns, valves and detector combinations. The solution to system design problems is easier to resolve than in the past.

Thereinabove, there will be described a plurality of preferred embodiments of the present invention, each using a combination of at least one elementary cell 22 having independently controlled ports 32, 34. For example, with reference to FIGS. 16A to 16D, as a first preferred variation, a real flow path equivalent like typical gas chromatographic six port valve could be realized. In this configuration, there still is sample flowing through the valve 84 on injection position. In this application, six elementary cells 22 are used, preferably extending on a circle 96 concentrical with the first interface 26. One of the controlled ports 32, 34 of a cell 22 is closed while the other is opened when the valve is not actuated. The chromatographic community is more familiar with this preferred valve embodiment and the resulting flow path. This preferred embodiment however introduces some dead volume. The fluid does not sweep the connecting conduits tied to common ports 36 when the corresponding ports are closed. Nevertheless, tests have been performed and show that this dead volume does not change the analytical results because of its small size. This assumption is correct for gaseous applications but may not be correct if the fluid is a liquid.

Figure 16A:
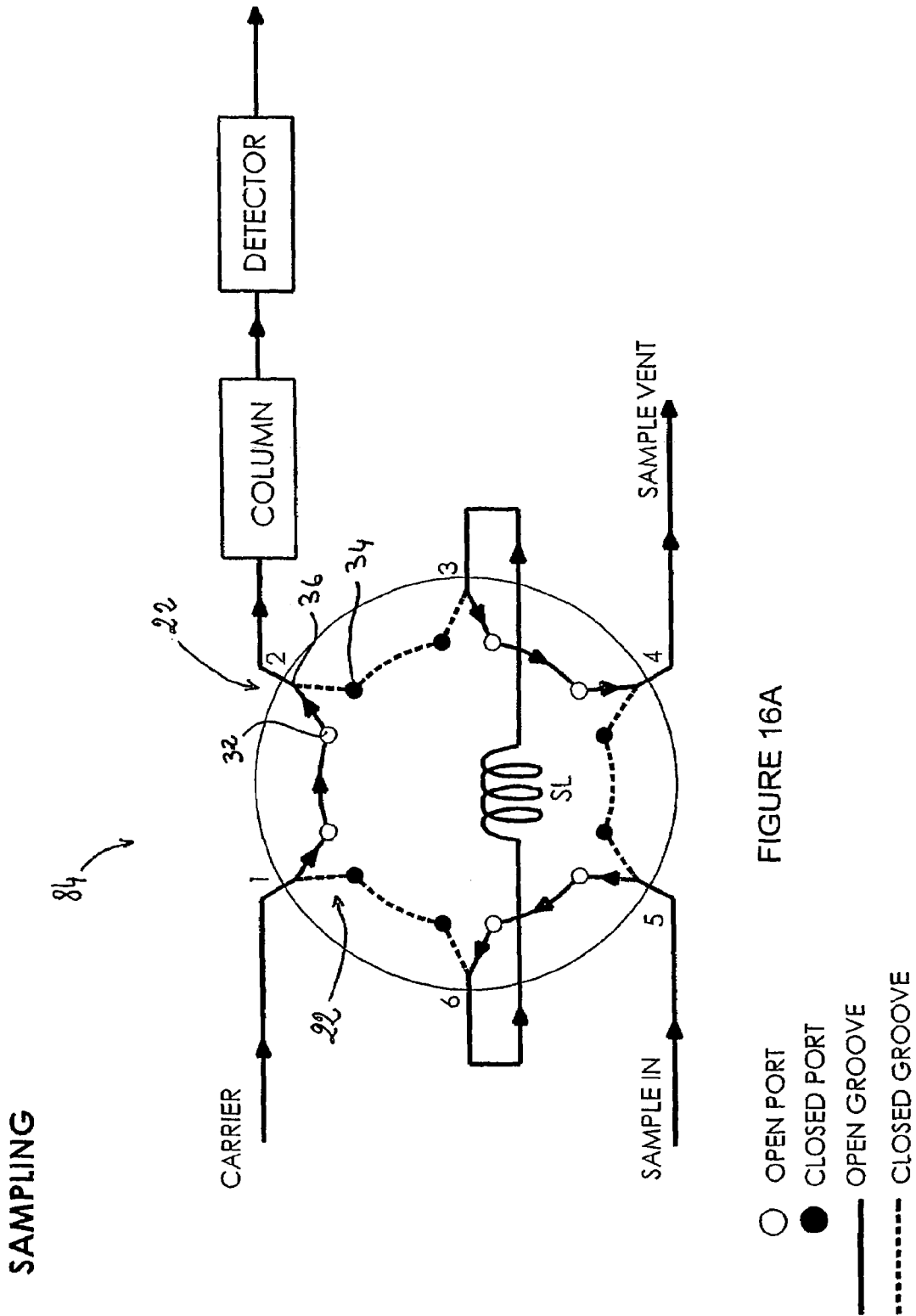
FIG. 16A is a schematic representation of another preferred embodiment of the diaphragm-sealed valve of the present invention, the valve being in the sampling position.
Figure 16B:
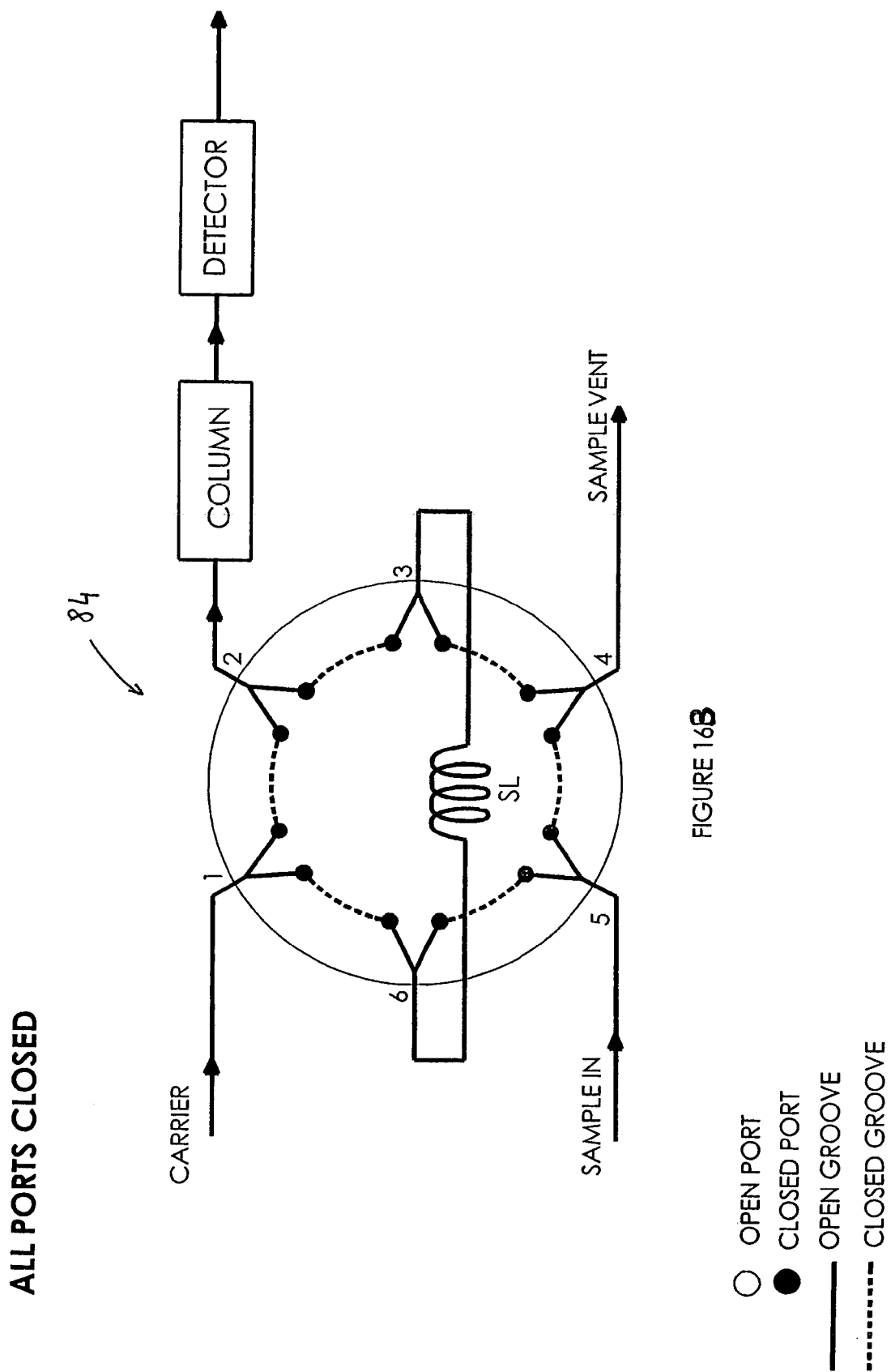
FIG. 16B is a schematic representation of the valve shown in FIG. 16A, the valve being in the intermediate position.
Figure 16C:
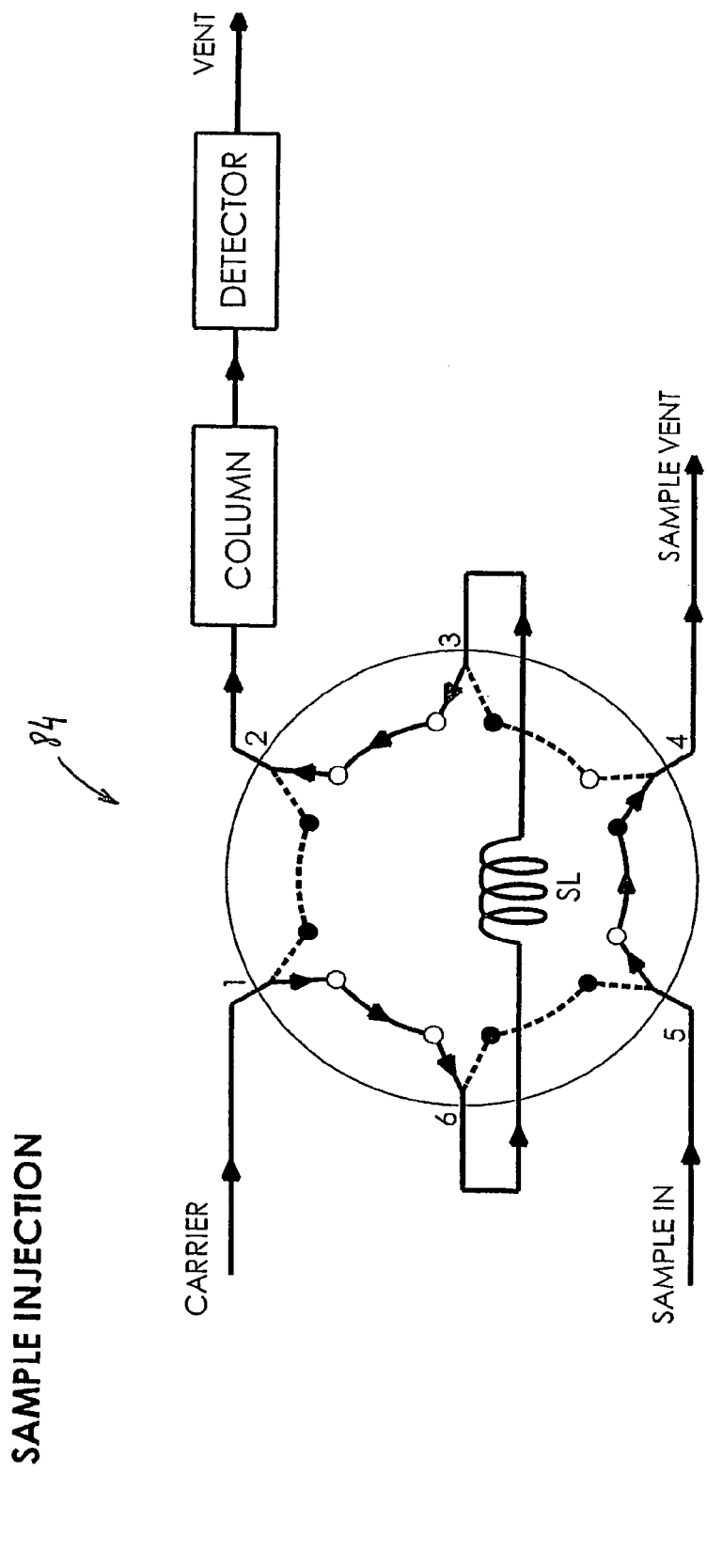
FIG. 16C is a schematic representation of the valve shown in FIG. 16A, the valve being in the sample injection position.

FIGS. 16A to 16C show different valve positions of a conventional injection cycle. It is obvious for people involved in the art that any number of elementary cells 22 can be embedded on the same substrate, which is preferably circularly or rectangularly shaped to provide the appropriate number of ports required for a particular application. It is also evident that even a four port valve could be realized. Presently, there are no four port gas chromatographic diaphragm valves available on the market. There are only four port rotary gas chromatographic valves. It is also evident that the valves may also be installed in a system that monitors the quality of the purging gas flowing in the circulation line 68 for diagnostic purposes, as shown in FIG. 16D and as already explained. Besides, in the case the valve is a rotary one, when the rotor is actuated, the purging circulation line in the rotor quickly passes over the stator's port. It doesn't change or hurt the analytical result but it requires time synchronization of the purity detector used to measure the quality of the purging gas for valve diagnostic. With the valve 84 of the present invention, when the ports 32, 34 are actuated, the purging circulation line 68 is never in contact with the fluid carrier or sample fluid. So, no synchronization of the purity detector is required and continuous measurements can be done, resulting in a continuous monitoring of valve performance. This characteristic is an important one of the present invention since it can not be obtained with the valves of the prior art.

As described above, in a preferred embodiment, the actuating mechanism is advantageously provided with a plurality of electrical solenoids, each actuating a corresponding one of the plurality of plungers. It should however be understood that any other convenient means to actuate the plungers could also be envisaged. For example, if the fluid pressure is relatively low, like in most of gaseous applications, simple solenoid valves could advantageously be used. For a medium pressure range, the actuating mechanism could advantageously be pneumatic. For high pressure range, a mechanical actuation could be envisaged.

Figure 18:
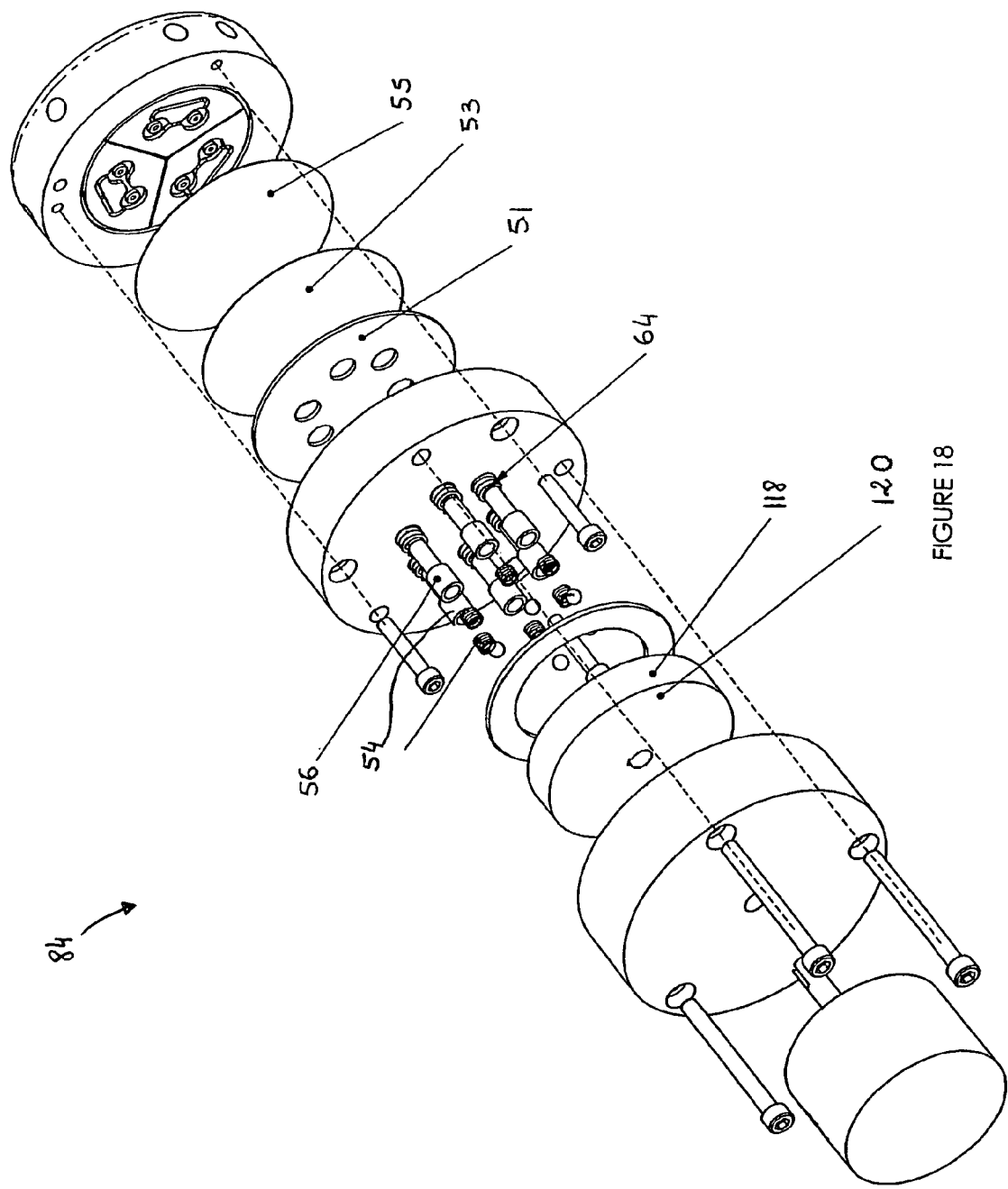
FIG. 18 is an exploded perspective view of another preferred embodiment of the diaphragm-sealed valve of the present invention.
Figure 19A:
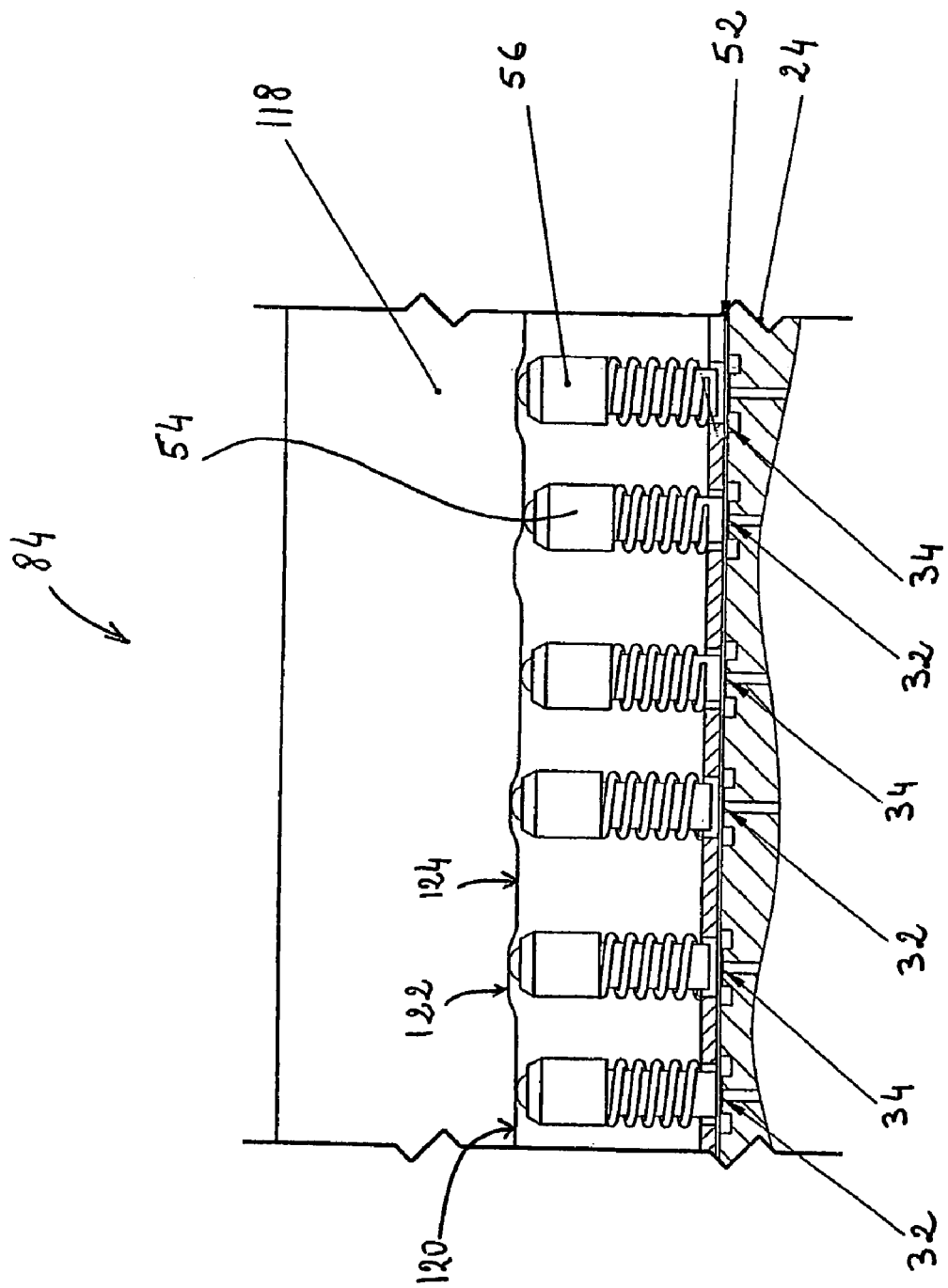
FIG. 19A is a partial cross-sectional side view of the valve shown in FIG. 18, the valve being in the sampling position.
Figure 19B:
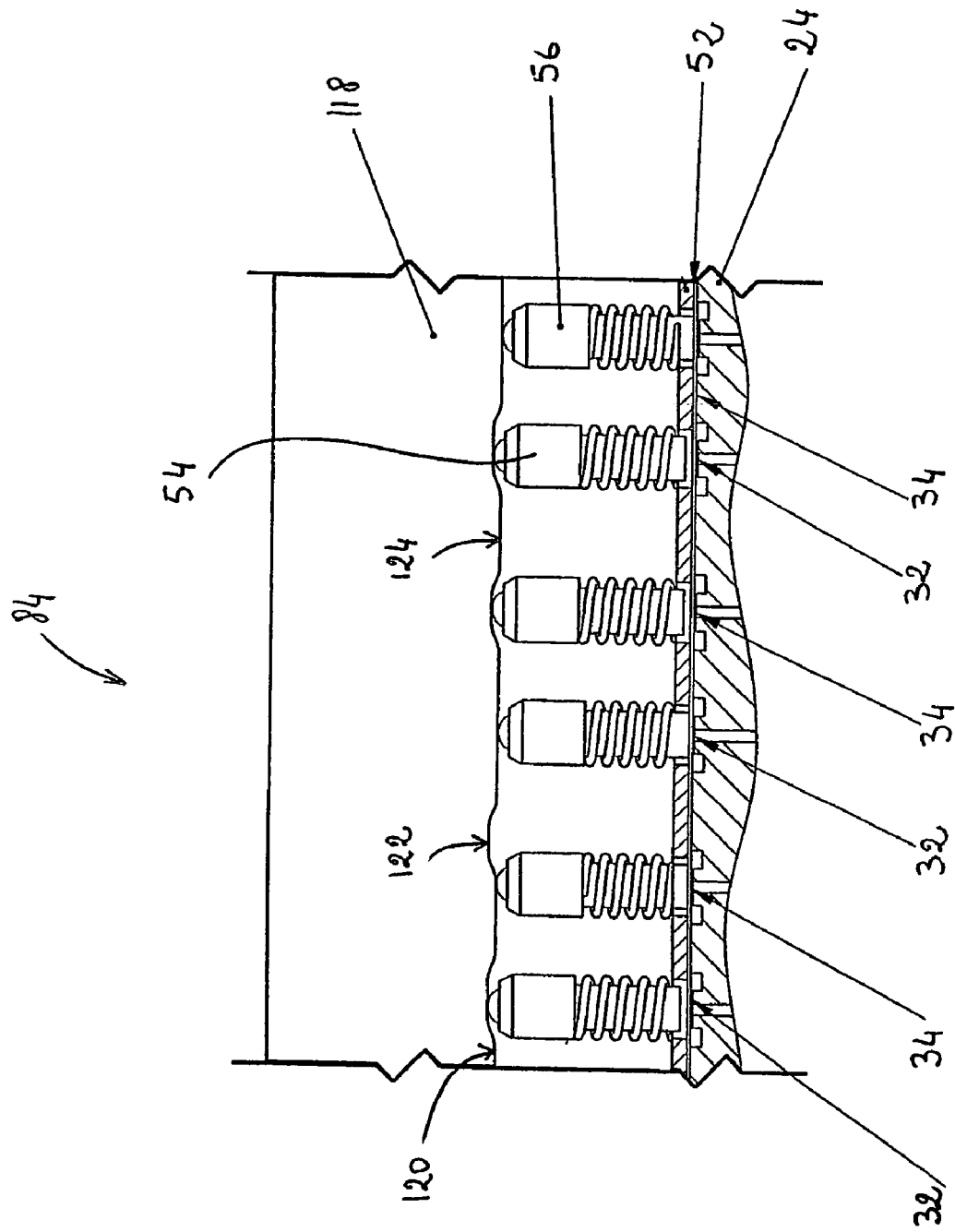
FIG. 19B is a partial cross-sectional side view of the valve shown in FIG. 18, the valve being in the intermediate position.
Figure 19C:
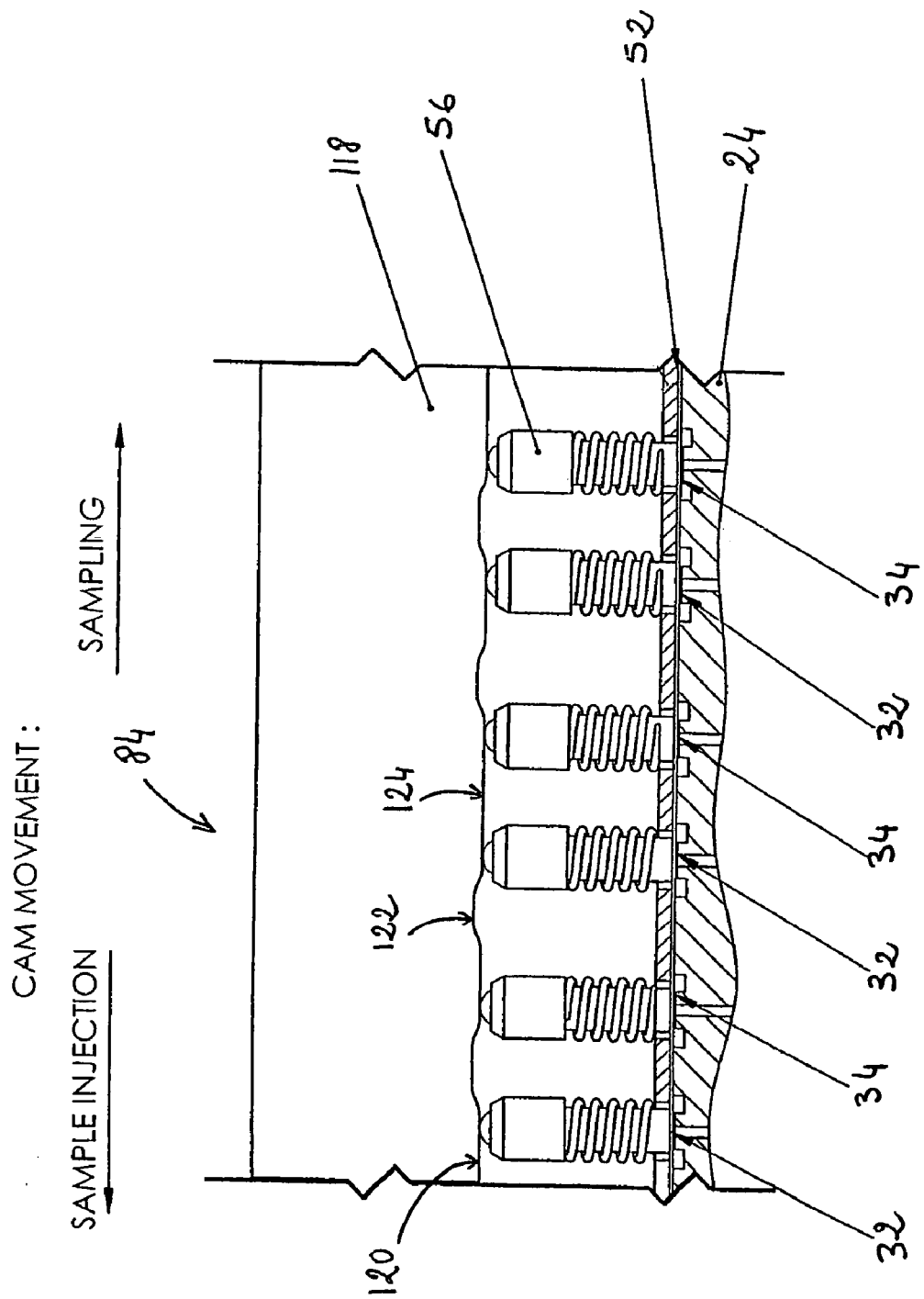
FIG. 19C is a partial cross-sectional side view of the valve shown in FIG. 18, the valve being in the sample injection position.

Accordingly, with reference to FIGS. 18 to 19C, in a further preferred embodiment of the valve 84, the actuating means can advantageously be based on a rotary cam 118 dedicated to synchronize the actuation of each of the plungers 54, 56. In this case, the actuating means is advantageously provided with a rotary cam 118 having a cam interface 120 in contact relationship with each of the plungers 54, 56. The cam interface 120 has a plurality of recessed portions 122 and a plurality of protuberant portions 124 particularly arranged and slidable against each of the plungers 54, 56 for actuating each of the plungers in a respective one of the closed and open positions thereof. Such actuating means has been proved to be very efficient.

Figure 17:
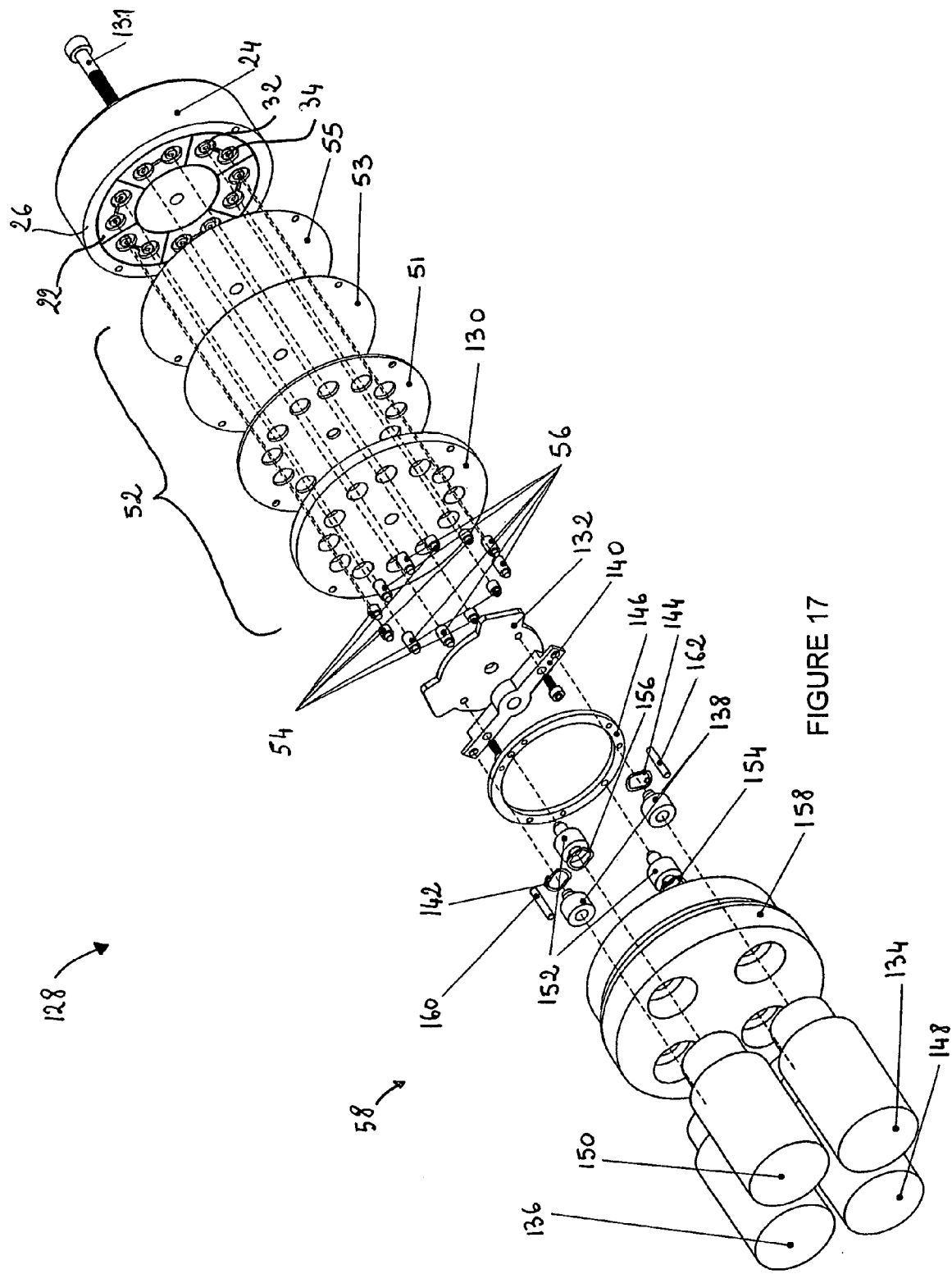
FIG. 17 is an exploded perspective view of the diaphragm-sealed valve shown in FIG. 16D.

FIG. 17 illustrates another preferred embodiment. This valve 128 is provided with six elementary switching cells 22 for allowing the flow path shown in FIG. 16A. The seal member 52 advantageously has a sealing plate 130 attached to the first body 24 for holding the Teflon spacer 51, the metallic diaphragm 53 and the polymer diaphragm 55 therebetween. Indeed, the sealing is performed when the sealing plate 130 is screwed on the first body 24 with screw 131. Of course any other convenient attaching means could also be envisaged. When the sealing plate 130 is screwed, it compresses the Teflon spacer 51, the stainless diaphragm 53 and the polymer diaphragm 55 against the first interface 26 of the first body 24. The compression force creates the sealing. As previously described, the port closing is achieved by pushing a plunger on the metallic diaphragm 53, preferably a stainless diaphragm, which compresses the polymer diaphragm 55 on the valve body's port. To make this valve properly working, it must be actuated with two independent actuators. These actuators are particularly designed to put the valve 128 in three different positions such as the sampling mode position (as illustrated in FIG. 16A), all ports closed or the intermediate position (as illustrated in FIG. 16B), and the sample injection position (as illustrated in FIG. 16C). Moreover, the valve 128 may advantageously be provided with a specially designed electronic circuit (not shown) for controlling the actuators. Thus, it can be possible to determine precisely the intermediate position's duration. This way, the valve operator will always be sure that all valve's port will never be opened at the same time to prevent unwanted communication between some ports. In this preferred embodiment, a particularly advantageous arrangement for actuating each of the ports 32, 34 is used. Indeed, each of the first plungers 54 has a predetermined first length while each of the second plungers 56 has a predetermined second length longer than the first length. The actuating means 58 is provided with a first independent actuator for actuating each of the first plungers 54 and a second independent actuator for actuating each of the second plungers 56 respectively. The first actuator has a short plungers push plate 132 adapted for pressing down each of the first plungers 54. The first actuator is further provided with first and second solenoids 134, 136 particularly arranged for acting against the short plungers push plate 132 to actuate each of the first plungers 54. In a preferred embodiment, the solenoids 134, 136 advantageously push on couplings 138, which push on a link 140, which sits on the short plungers push plate 132. The short plunger push plate 132 is pushing on short plungers 54. The ports controlled with this first actuator are normally opened. This position is insured by the wave springs 142 and 144. The second actuator is provided with a long plungers push element 146 coaxial to the short plungers push plate 132 and adapted for pressing down each of the second plungers 56. Preferably, the long plungers push element 146 is ring shaped. The second actuator further has first and second solenoids 148, 150 particularly arranged for acting against the long plungers push element 146 to actuate each of the second plungers 56. Indeed, the solenoids 148, 150 push on couplings 152 which are able to act on the long plungers pushing element 146. The pushing ring 146 pushes on the long plungers 56. The ports controlled with this second actuator are normally closed. This position is insured by the wave springs 154 and 156. Preferably, each of the solenoids 134, 136, 148, 150 is fixed on a solenoid support 158. Also preferably, the overall alignment of the valve is insured by dowel pins 160 and 162.

Figure 20A:
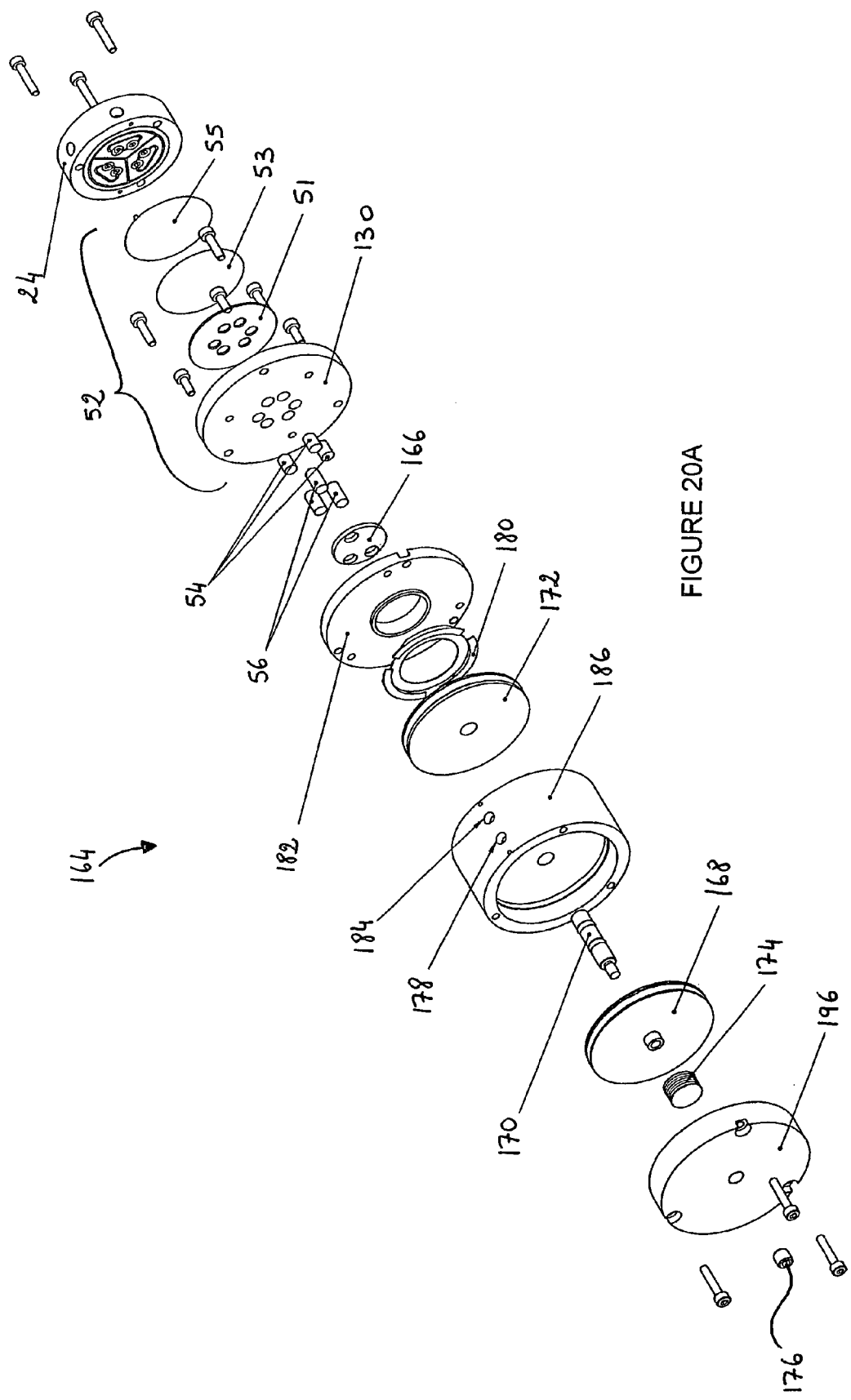
FIG. 20A is an exploded perspective view of another preferred embodiment of the diaphragm-sealed valve of the present invention.
Figure 20B:
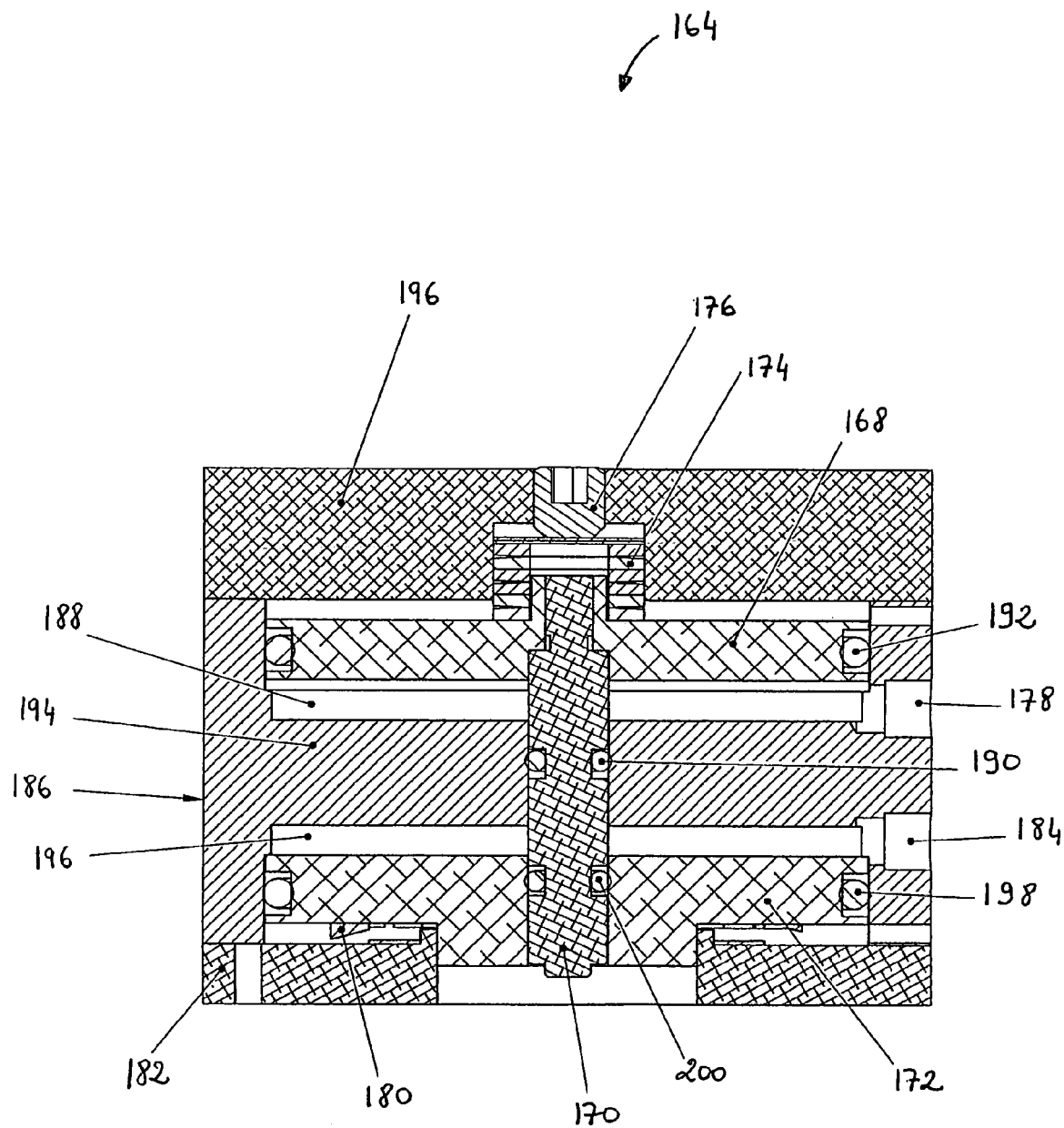
FIG. 20B is a cross sectional view of the valve actuator shown in FIG. 20A.

FIGS. 20A and 20B illustrate a valve 164 according to another preferred embodiment of the present invention. The first body 24 of this valve 164 is the same as the one described with reference to FIGS. 10A to 10G. The actuating means 58 is particularly designed to put the valve in three different positions such as the sampling mode position (as illustrated in FIG. 10B), all ports closed or the intermediate position (as illustrated in FIG. 10D), and the sample injection position (as illustrated in FIG. 10F). This valve 164 is actuated with concentric actuators, preferably pneumatic actuators. To make this valve properly working, it must be actuated with two independent actuators. Moreover, the valve 164 may advantageously be provided with a specially designed electronic circuit (not shown) for controlling the actuators. Thus, it can be possible to determine precisely the intermediate position's duration. This way, the valve operator will always be sure that all valve's port will never be opened at the same time to prevent unwanted communication between some ports. In this preferred embodiment, a particularly advantageous arrangement for actuating each of the ports 32, 34 is used. Indeed, each of the first plungers 54 has a predetermined first length while each of the second plungers 56 has a predetermined second length longer than the first length. The actuating means 58 has a first concentric actuator for actuating each of the first plungers 54 and a second concentric actuator for actuating each of the second plungers 56. Preferably, the first and second concentric actuators are pneumatic. The first actuator is provided with a short plungers push plate 166 for pressing down each of the first plungers 54. The first actuator further has an upper piston 168 and a shaft 170 particularly arranged for acting against the push plate 166 to actuate each of the first plungers 54. The second actuator has a lower piston 172 extending around the shaft 170 for pressing down each of the second plungers 56. The port closing pattern is the same as the one described with reference to FIG. 10B. The second plungers 56, which are the long plungers, are used to commute the ports numbered 3, 6 and 9 in FIG. 10B. The first plungers 54, which are the short plungers, are used to commute the ports numbered 2, 4 and 7. To prevent any problem with a lack of actuation gas pressure, the ports 2, 4 and 7 are preferably normally closed. This is made possible by the use of a Belleville washer stack 174 and a compression set screw 176. The Belleville washer stack 174 sits on the upper piston 168 on which the upper piston shaft 170 is screwed. This shaft 170 pushes the short plunger push plate 166 when the upper piston 168 is not actuated. The upper piston 168 is actuated when air is supplied to the upper cylinder port 178. When the upper piston 168 is actuated, the ports 2, 4 and 7 are opened. The second actuator, which is provided with the lower piston 172, also preferably has a finger spring 180. This second actuator makes ports 3, 6, and 9 normally opened. The finger spring 180 ensures that the lower piston 172 doesn't act on the long plungers 56 when the lower piston 172 is not actuated. The finger spring 180 sit on the actuator's lower cap 182, which is fixed on the sealing plate 130. When pressurized gas is supplied through the lower cylinder port 184, it pushes the lower piston 172 down which, by the way, acts on the long plungers 56 to close ports 3, 6 and 9. The actuation air is preferably controlled with a specially designed electronic circuit and solenoid valves (not shown). FIG. 20B shows a sectional view of the pneumatic actuator assembly and clearly illustrates how the upper and lower pistons 168, 172 are assembled in a cylinder 186. In this preferred embodiment, to obtain two independent actuators, two different air chambers must be included in the actuator. The upper piston air chamber 188 is sealed with O-Ring 190 and 192, upper piston 168 and the cylinder middle section 194. The actuation air is supplied through port 178. The normally closed position of this actuator is insured by the Belleville washer stack 174 and the compression set screw 176 screwed in the actuator's upper cap 196. The lower piston air chamber 196 is sealed with O-Ring 198 and 200, lower piston 172 and the cylinder middle section 194. The actuation air is supplied through port 184. The normally open position is insured with finger spring 180, which sits on the actuator lower cap 182.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A diaphragm-sealed valve comprising:
  a first body having a first interface provided with a recessed fluid communication channel extending therein, said first body having a first, a second and a common fluid port, each of said ports opening into said recessed fluid communication channel for interconnecting each of said ports together through said fluid communication channel, each of said first and second ports being provided with a seat disposed so as to allow fluid communication therearound within said communication channel;
  a second body interconnected with said first body and having a second interface facing said first interface, said second body having a first and a second passage, each of said passages facing one of said first and second ports respectively;
  a seal member compressibly positioned between said first and second interfaces, said seal member having a shape adapted to cover said first and second ports, said seal member comprising a Teflon spacer, a metallic diaphragm and a polymer diaphragm, each being arranged in a stacked relationship, said polymer diaphragm being pressable against the seat of each of the first and second ports;
  a first and a second plunger, each being respectively slidably disposed in one of said passages of said second body, each of said plungers having a closed position wherein the corresponding plunger presses down the seal member against the seat of the corresponding port for closing said corresponding port, and an open position wherein said plunger extends away from the seat of the corresponding port for allowing a fluid communication between the corresponding port and said channel; and
  actuating means for actuating each of said plungers between said closed and open positions thereof.

2. The diaphragm-sealed valve according to claim 1, wherein said actuating means independently actuate each of said plungers.

3. The diaphragm-sealed valve according to claim 1, wherein each of said first and second interfaces has a planar shape.

4. The diaphragm-sealed valve according to claim 1, wherein the seat of each of said first and second ports comprises a raised portion.

5. The diaphragm-sealed valve according to claim 1, wherein said fluid communication channel comprises a loop-shaped portion.

6. The diaphragm-sealed valve according to claim 1, wherein the shape of the seal member is adapted to cover said fluid communication channel.

7. The diaphragm-sealed valve according to claim 1, wherein said seal member comprises a polymer disc.

8. The diaphragm-sealed valve according to claim 1, wherein said seal member further comprises a sealing plate attached to the first body for holding said Teflon spacer, said metallic diaphragm and said polymer diaphragm therebetween.

9. The diaphragm-sealed valve according to claim 1, wherein each of said plungers is attached to said seal member.

10. The diaphragm-sealed valve according to claim 1, wherein said actuating means comprise a first and a second solenoid, each respectively actuating one of said plungers.

11. The diaphragm-sealed valve according to claim 10, wherein said actuating means further comprise first and second resilient means, each being respectively mounted on a corresponding plunger for biasing said corresponding plunger.

12. The diaphragm-sealed valve according to claim 1, wherein each of said plungers has a predetermined resting position providing a corresponding one of said closed and open positions.

13. The diaphragm-sealed valve according to claim 1, wherein said first plunger is normally in said open position while said second plunger is normally in said closed position.

14. The diaphragm-sealed valve according to claim 1, wherein the valve further comprises a purge circulation line comprising:
  an annular recess extending in said first interface and surrounding said fluid communication channel; and
  a fluid inlet and a fluid outlet, each having an opening lying in said annular recess for providing a continuous fluid flow in said annular recess.

15. An analytical chromatographic system comprising:
  a diaphragm-sealed valve as defined in claim 14; and
  monitoring means operatively connected to the fluid outlet for monitoring a fluid passing therethrough.

16. The analytical chromatographic system according to claim 15, wherein said monitoring means comprise a purity detector for detecting contamination of said fluid.

17. The analytical chromatographic system according to claim 15, wherein said monitoring means are adapted to monitor said fluid continuously.

18. A diaphragm-sealed valve comprising:
  a first body having a first interface provided with a plurality of distinct recessed fluid communication channels extending therein, said first body having a plurality of port sets, each comprising a first, a second and a common fluid port, each port of a corresponding set opening into a corresponding one of said recessed fluid communication channels respectively for interconnecting each port of said corresponding set together through said corresponding fluid communication channel respectively, each of said first and second ports of each of said sets being provided with a seat disposed so as to allow fluid communication therearound within said corresponding communication channel;
  a second body interconnected with said first body and having a second interface facing said first interface, said second body having a plurality of passage pairs, each comprising a first and a second passage, each passage of a corresponding pair respectively facing one of said first and second ports of a corresponding set;
  a seal member compressibly positioned between said first and second interfaces, said seal member having a shape adapted to cover each of said first and second ports of all of said port sets, said seal member comprising a Teflon spacer, a metallic diaphragm and a polymer diaphragm, each being arranged in a stacked relationship, said polymer diaphragm being pressable against the seat of each of the first and second ports;

a plurality of pairs of first and second plungers, each plunger of a corresponding pair being respectively slidably disposed in one of said passages of a corresponding pair, each of said plungers having a closed position wherein the corresponding plunger presses down the seal member against the seat of the corresponding port for closing said corresponding port, and an open position wherein said plunger extends away from the seat of the corresponding port for allowing a fluid communication between the corresponding port and a corresponding channel; and actuating means for actuating each of said plungers between said closed and open positions thereof.

19. The diaphragm-sealed valve according to claim 18, wherein the valve further comprises a purge circulation line comprising:

a looped recessed fluid circuit extending in said first interface, said looped fluid circuit comprising an outer annular recess and an inner recess, each extending in said first interface, said fluid circuit further comprising a plurality of separation recesses radially extending in said first interface, each of said separation recesses being connected to each of said inner and outer recesses for defining a plurality of first interface portions isolated from each others, each of said first interface portions enclosing one of said fluid communication channels; and a fluid inlet and a fluid outlet, each having an opening lying at said first interface, each of said inlet and outlet being in continuous fluid communication with a respective one of said inner and outer recesses for providing a continuous fluid flow in said looped recessed fluid circuit.

20. The diaphragm-sealed valve according to claim 18, wherein each of said first and second ports are circularly arranged in a port circle concentrical with said first interface.

21. The diaphragm-sealed valve according to claim 18, wherein said actuating means independently actuate each of said plungers.

22. The diaphragm-sealed valve according to claim 18, wherein said actuating means comprise a plurality of pairs of first and second solenoids, each solenoid of a corresponding pair respectively actuating a corresponding one plunger of a corresponding pair.

23. The diaphragm-sealed valve according to claim 18, wherein said actuating means comprise a rotary cam having a cam interface in contact relationship with each of said plungers, said cam interface comprising a plurality of recessed portions and a plurality of protuberant portions particularly arranged and slidable against each of said plungers for actuating each of said plungers in a respective one of said closed and open positions thereof.

24. The diaphragm-sealed valve according to claim 18, wherein each of said first plungers has a predetermined first length, each of said second plungers having a predetermined second length longer than said first length, said actuating means comprising a first concentric actuator for actuating each of said first plungers and a second concentric actuator for actuating each of said second plungers, said first actuator comprising a short plungers push plate for pressing down each of said first plungers, said first actuator further comprising an upper piston and a shaft particularly arranged for acting against the push plate to actuate each of said first plungers, said second actuator comprising a lower piston extending around said shaft for pressing down each of said second plungers.

25. The diaphragm-sealed valve according to claim 18, wherein each of said first plungers has a predetermined first length, each of said second plungers having a predetermined second length longer than said first length, said actuating means comprising a first and a second independent actuator for actuating each of said first plungers and each of said second plungers respectively, said first actuator comprising a short plungers push plate adapted for pressing down each of said first plungers, said first actuator further comprising first and second solenoids particularly arranged for acting against the short plungers push plate to actuate each of said first plungers, said second actuator comprising a long plungers push element coaxial to said short plungers push plate and adapted for pressing down each of said second plungers, said second actuator further comprising first and second solenoids particularly arranged for acting against the long plungers push element to actuate each of said second plungers.

* * * * *